(12) United States Patent
Alsuhaibani

(10) Patent No.: US 11,844,886 B2
(45) Date of Patent: Dec. 19, 2023

(54) SYRINGE WITH CONTROLLABLE BREAKING FEATURES

(71) Applicant: ALSAHAB MEDICAL COMPANY, Riyadh (SA)

(72) Inventor: Abdulaziz A. Alsuhaibani, Riyadh (SA)

(73) Assignee: ALSAHAB MEDICAL COMPANY, Riyadh (SA)

( * ) Notice: Subject to any disclaimer, the term of this patent is extended or adjusted under 35 U.S.C. 154(b) by 0 days.

(21) Appl. No.: 17/928,941

(22) PCT Filed: Jul. 2, 2021

(86) PCT No.: PCT/IB2021/055979
§ 371 (c)(1),
(2) Date: Dec. 1, 2022

(87) PCT Pub. No.: WO2022/009055
PCT Pub. Date: Jan. 13, 2022

(65) Prior Publication Data
US 2023/0191034 A1    Jun. 22, 2023

Related U.S. Application Data

(60) Provisional application No. 63/208,307, filed on Jun. 8, 2021, provisional application No. 63/048,481, filed on Jul. 6, 2020.

(51) Int. Cl.
*A61M 5/31* (2006.01)
*A61M 5/50* (2006.01)

(52) U.S. Cl.
CPC ........ *A61M 5/3148* (2013.01); *A61M 5/3137* (2013.01); *A61M 2005/3139* (2013.01); *A61M 2005/5006* (2013.01)

(58) Field of Classification Search
CPC .............. A61M 5/3148; A61M 5/3137; A61M 2005/3139; A61M 2005/5006
See application file for complete search history.

(56) References Cited

U.S. PATENT DOCUMENTS

| 5,004,460 | A | * | 4/1991 | Gimeno | ............... A61M 5/5066 604/110 |
| 5,591,131 | A | * | 1/1997 | Chen | ...................... A61M 5/322 604/110 |

(Continued)

FOREIGN PATENT DOCUMENTS

| EP | 1726321 A2 * | 11/2006 | ........ A61M 5/31511 |
| EP | 1726321 A2 | 11/2006 | |
| WO | 2020/113123 A1 | 6/2020 | |

OTHER PUBLICATIONS

International Search Report and Written Opinion dated Oct. 5, 2021, received for PCT Application PCT/IB2021/055979, filed on Jul. 2, 2021, 11 pages.

*Primary Examiner* — Amber R Stiles
*Assistant Examiner* — Hong-Van N Trinh
(74) *Attorney, Agent, or Firm* — XSENSUS LLP

(57) ABSTRACT

A syringe with structural features to accomplish one-handed aspiration as well as one-handed injection. The syringe includes one or more breaking points that are configured to break at predetermined locations in response to external forces being applied thereto. To assist in accountability, identification chips and/or codes are included to allow for the traceability of the syringe to potential sources of irresponsible dispensing of medical waste.

16 Claims, 23 Drawing Sheets

(56) References Cited

U.S. PATENT DOCUMENTS

| | | | | |
|---|---|---|---|---|
| 6,953,449 B2* | 10/2005 | Huang | ............... | A61M 5/3135 |
| | | | | 604/218 |
| 2003/0212367 A1* | 11/2003 | Shue | ................... | A61M 5/322 |
| | | | | 604/196 |
| 2007/0073245 A1* | 3/2007 | Shih | ..................... | A61M 5/322 |
| | | | | 604/110 |
| 2012/0191041 A1* | 7/2012 | Pullara | ............... | A61M 5/5066 |
| | | | | 604/110 |
| 2014/0221923 A1* | 8/2014 | Bai | ................... | A61M 5/5066 |
| | | | | 604/110 |
| 2016/0166772 A1 | 6/2016 | Mirzazadeh et al. | | |
| 2017/0056292 A1 | 3/2017 | Biermann et al. | | |
| 2018/0296804 A1 | 10/2018 | Bierman | | |
| 2019/0355463 A1 | 11/2019 | Gardner | | |
| 2020/0113587 A1* | 4/2020 | Garrison | ............... | A61B 17/22 |

* cited by examiner

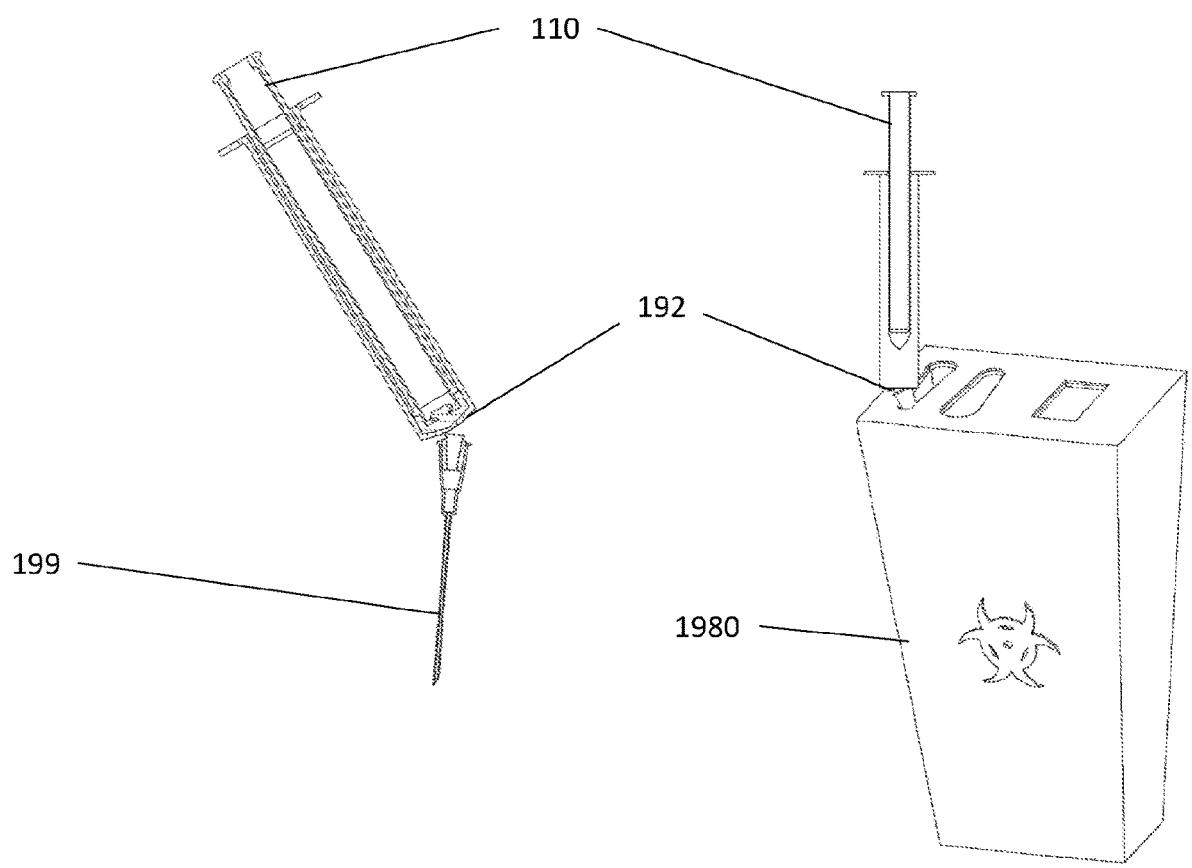

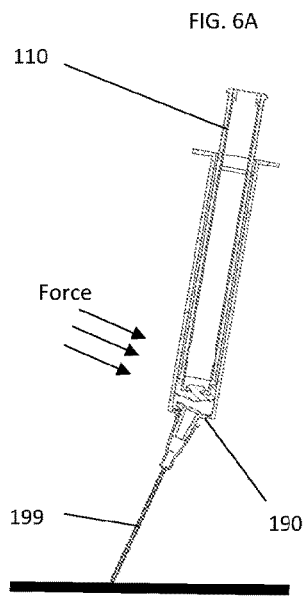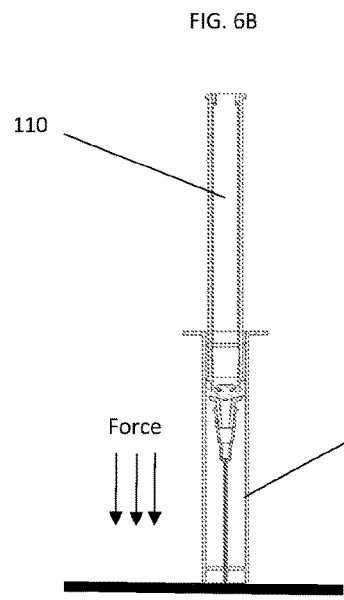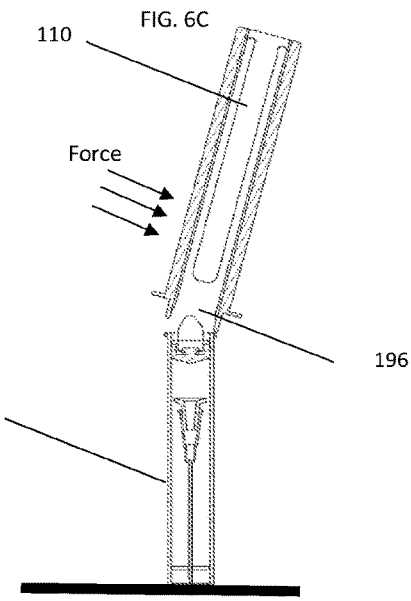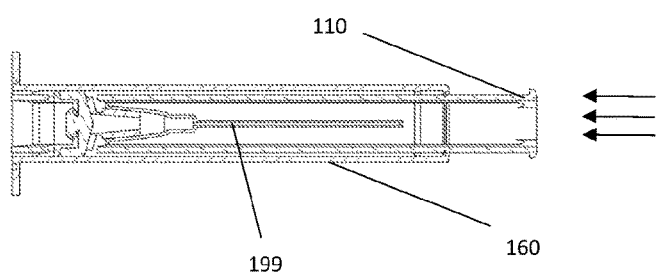

1900

261

SYRINGE WITH CONTROLLABLE BREAKING FEATURES

CROSS REFERENCE TO RELATED APPLICATIONS

The present application is based on PCT filing PCT/IB2021/055979, filed Jul. 2, 2021, which claims the benefit of the earlier filing dates of U.S. provisional application 63/048,481, filed Jul. 6, 2020, and U.S. provisional application 63/208,307, filed Jun. 8, 2021, the entire contents of each of which being incorporated herein by reference.

BACKGROUND

Technical Field

The present disclosure generally relates to syringes, more particularly to medical syringes. Additionally, it also relates to the field of medicine, including medical devices, as well as other fields where syringes may be used for one time in aspiration and injection modes of operation. The present disclosure further relates to syringes that have controlled breakpoints, that allow for disposal of used syringes in a socially responsible way that minimizes unauthorized secondary use of the syringes.

Description of the Related Art

Medical syringes are used in both injection and aspiration modes. Conventionally, when a syringe is used to inject medicine (or other fluids) via a needle into a vein or the like, the operator holds the syringe in one hand and squeezes the plunger into the syringe cylinder using the thumb and fingers of the same hand. However, when a syringe is used to aspirate or withdraw blood or other fluid from a needle inserted in a vein or the like, the operator uses two hands, typically holding the cylinder in one hand while pulling the plunger out of the cylinder with the other hand.

Specialty syringes have been made with a retractable needle shield that is capable of being retracted to expose the needle for use. After using the needle, a needle shielding position, if desired, is configured to be removed from the syringe with the shielded needle safely contained within the retractable needle shield via a frangible segment between the syringe barrel and the needle shield components. With an elongated generally tubular needle shield advanced distally and optionally locked to a collar, the operator may apply a force in a direction perpendicular to the longitudinal axis of the elongate generally tubular needle shield sufficient to break the safety syringe at the at least partially relieved proximal region between a barrel and the elongate generally tubular needle shield. This separates the used hollow needle component from the barrel/plunger component to allow separate disposal of the respective components in an approved medical waste container.

As recognized by the present inventor, there are several suboptimal features about conventional syringes that are used for both injection and aspiration, as well as adapters that assist in aspiration. First, in conventional injection mode, an operator normally clamps the barrel of the syringe between the operator's index finger and the middle finger, while depressing the plunger with the operator's thumb. However, a different gripping action is used for aspiration. Typically, aspiration is performed with two hands, one holding the body of the syringe, while the other grips the end of the plunger and withdraws the plunger from the body of the syringe. Two-handed operation is not ideal because the operator may need to use their other hand for another task, such as holding a bottle while withdrawing a sample. Additionally, having an unoccupied hand while performing surgical procedures is also extremely beneficial due to the nature of unpredictability in said procedures. The present inventor also recognized the advantages of disposing the syringes safely and disabling them to prevent their re-use. However, because the conventional syringe often requires the use of two-hands, the attending physician cannot adequately and safely handle the syringe properly when discarding it safely.

SUMMARY

As recognized by the present inventor, there is a need for a syringe that can easily be purposefully broken after a single use in order to reduce the risk of transmission of bloodborne diseases from needle injuries. Various embodiments are described of a disposable syringe that prevents re-use. Inner arms are configured to provide controlled breakability to an inner part of the plunger inside the syringe cavity. The syringe is configured to allow for a one-handed operation; aspiration or injection operation, while freeing the other hand to assist in a medical procedure. Once it has been used for its intended purpose, the syringe may be purposefully broken at different locations to prevent reuse. For example, an operator may hold the barrel while breaking a plunger of the syringe. In addition, the frontal part of syringe's barrel is controllably breakable as well. By providing the breakable features in the subject syringe, an operator can break the syringe after use, and broken in a particular way so as to avoid inadvertent injury to the physician or a person disposing of medical waste. Breaking the syringe prevents an unauthorized user from subsequently obtaining the once-used syringe, perhaps by combing through medical waste, and re-using the syringe for nefarious purposes, such as injecting illegal drugs.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 5 is a side view of a cross-section of a syringe and a sharps container, showing how the syringe in the first embodiment may be controllably broken at nozzle breaking point into the sharp's container.

FIGS. 6A, 6B, 6C and 6D show respective configurations of the syringe of the first embodiment in four different steps during breaking and self-containment of the syringe to permit safe disposal.

FIG. 9A shows the 2-part plunger in an extended state; FIG. 9B shows the 2-part plunger in an retracted state; and FIG. 9C shows a rear view of the syringe according to a third embodiment.

DETAILED DESCRIPTION

Figure 1:
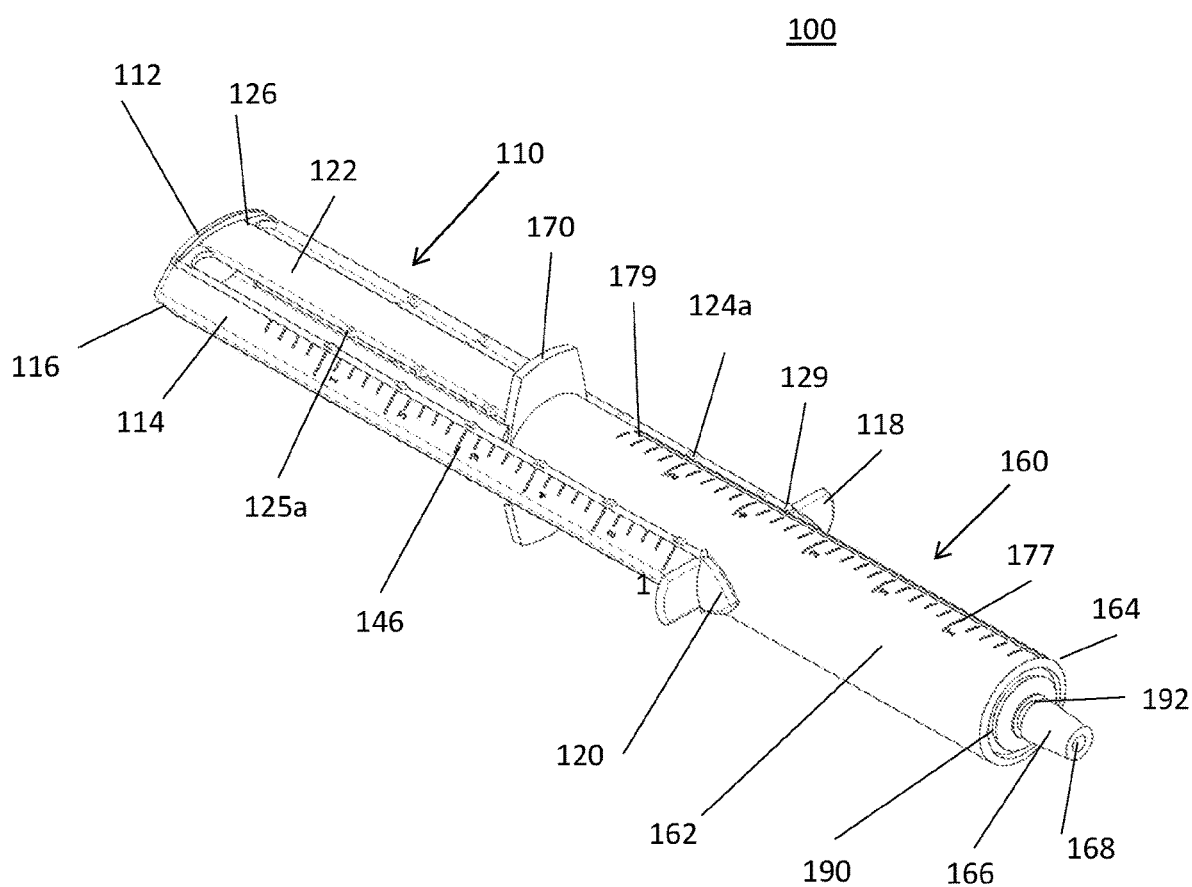
FIG. 1 is a perspective view of a syringe with dual inner arms for single-handed aspiration/injection use of the syringe, according to a first embodiment.

As used herein, an element or step recited in the singular and proceeded with the word "a" or "an" should be understood as not excluding plural elements or steps, unless such exclusion is explicitly recited. Furthermore, references to "one embodiment" of the present disclosure are not intended to be interpreted as excluding the existence of additional embodiments that also incorporate the recited features.

The present inventor identified several suboptimal features about conventional syringes that are used for both injection and aspiration, as well as adapters that assist in aspiration. First, the inventor recognized that in conventional injection mode, operators normally clamp the barrel of the syringe between the operator's index finger and the middle finger, while depressing the plunger with the operator's thumb. However, a different gripping action is used for aspiration. Typically, aspiration is performed with two hands, one holding the body of the syringe, while the other grips the end of the plunger and withdraws the plunger from the body of the syringe. Two-handed operation is not ideal because the operator may very well want to use their other hand for another task, such as holding a bottle while withdrawing a sample. Also, if another person holds the bottle for the operator, there is a third hand in the operation scene which made interfere with the operator's ability to fully see the operation scene.

The present inventor also recognized the advantages of disposing the syringes safely and disabling them to prevent their re-use. However, because the conventional syringe often requires the use of two-hands, the attending physician cannot adequately and safely handle the syringe properly when discarding it safely.

In light of the recognition of this problem, and other problems, the present inventor recognized the practical value in a syringe system that, in addition to enabling a singled-handed injection/aspiration function, also incorporates controllable breaking features that allow the attending physician to safely discard and disable the syringe after its use. Moreover, the present inventor recognized the value in having a safety syringe system that permits the physician to use a single hand to break the one-handed syringe after using it, to disable its usage.

The present inventor also recognized the benefit of including a computer-based control system (e.g., via application of a trained artificial intelligence model) for controlling information specific to a particular syringe that may be used to control an operation and/or disposal of the particular syringe. In one example, an information item (such as a semiconductor memory, RFID chip, and/or machine readable optical code, such as a QR or bar code, may be used to obtain a technical specification for the syringe, and use the technical specification's contents to control an operation of another device, such as an infusion pump to precisely regulate a contents of a syringe when used for dispensing a liquid from the syringe as part of a medical treatment. This computer-based reading of the content regarding the syringe may also be used to help minimize variations in syringe volumes according to variations in manufacturing processes used by different manufacturers. Furthermore, the information about the syringe may be used to be matched to a patient profile, as well as their medical record, so, for example, traceability regarding the use of the syringe may be helpful in diagnosing potential inadvertent administration of materials to the patient. Furthermore, the identification for the syringe may be used to correlate the origin of other syringes that have been detected as being improperly disposed of so the source of the improper disposals may be identified and then confronted.

Figure 2:
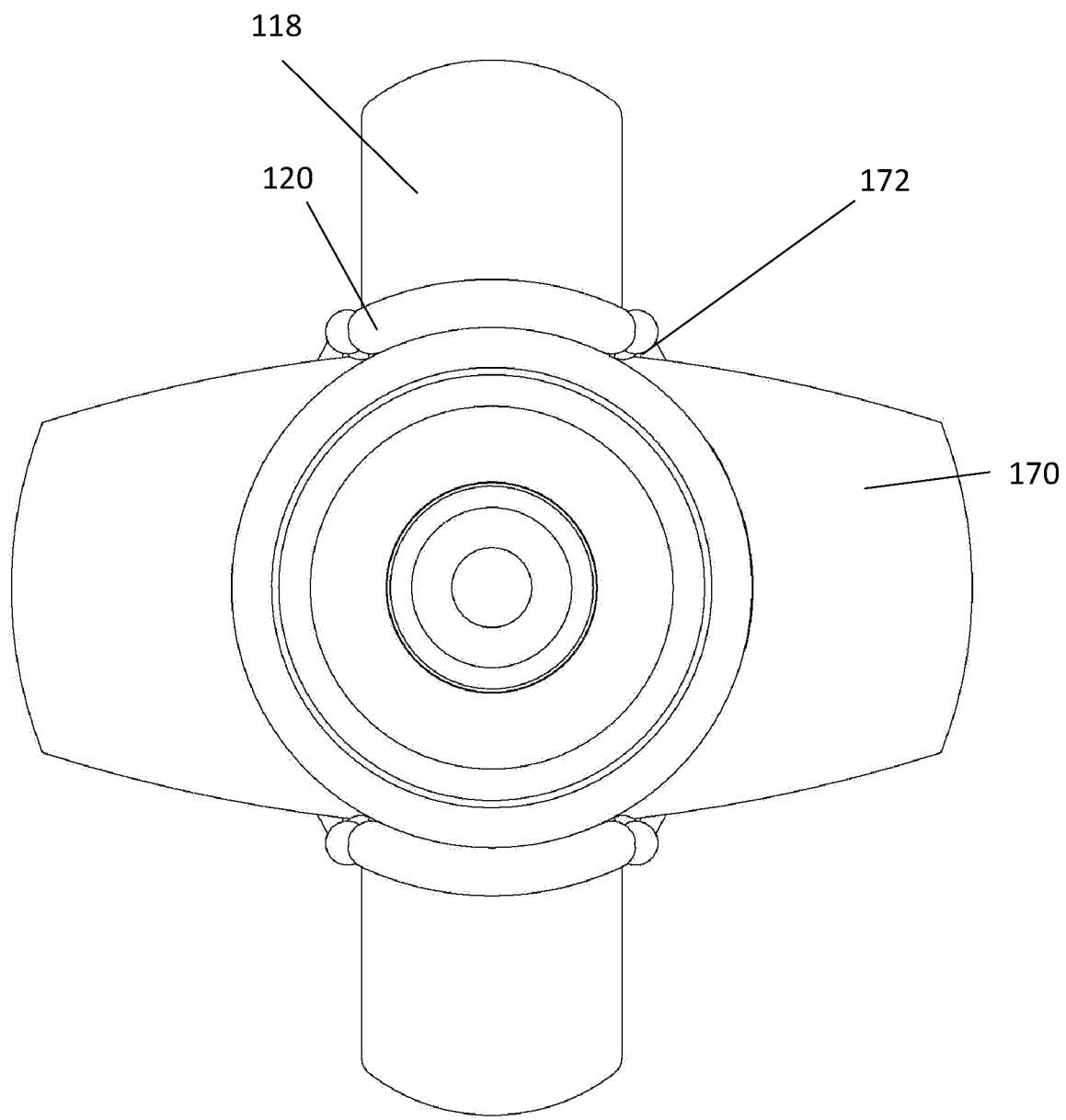
FIG. 2 is a front view of the syringe shown in FIG. 1.
Figure 3:
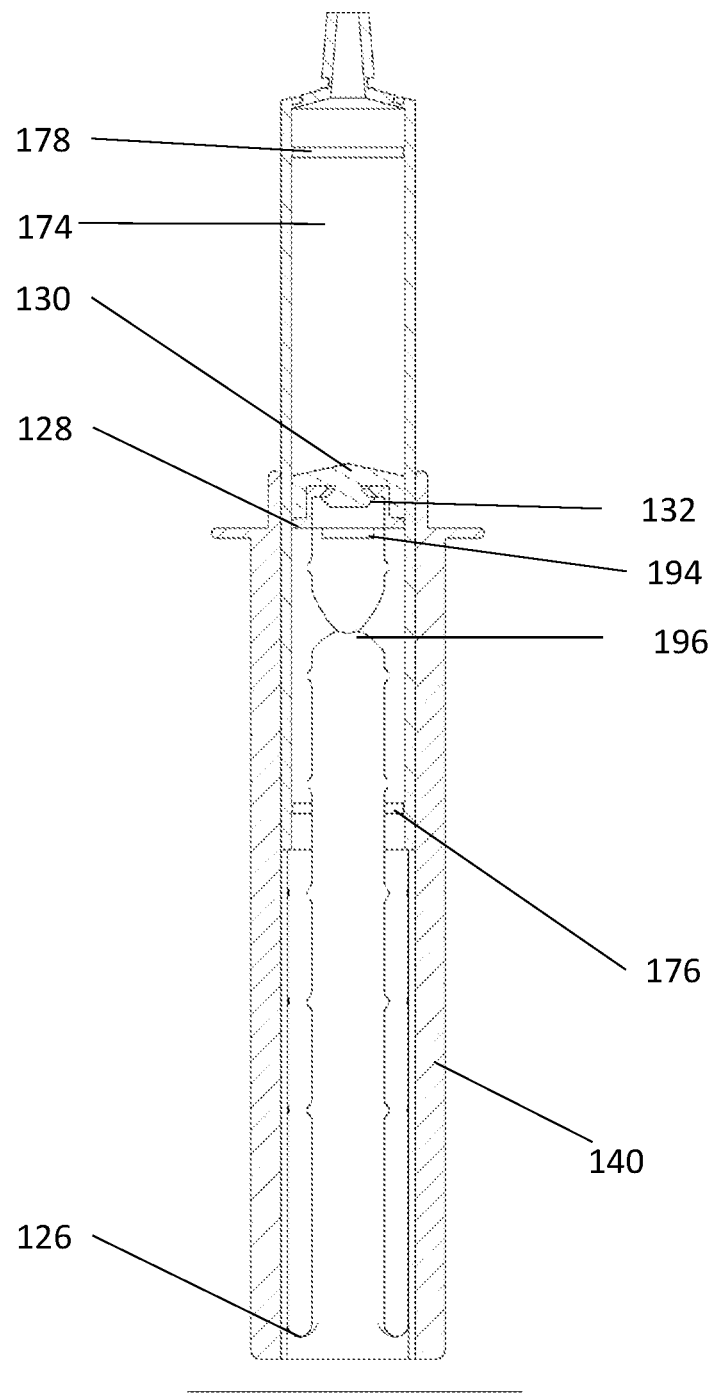
FIG. 3 is a longitudinal cross-sectional view of the syringe shown in FIG. 1 along a central longitudinal axis.

Referring now to the drawings, wherein like reference numerals designate identical or corresponding parts throughout the several views, FIGS. 1 to 4 illustrate a syringe 100 for single-handed injection/aspiration operation. The syringe 100 includes a plunger 110, a barrel 160, each with various subcomponents as will be discussed. If a needle is affixed to the barrel 160, a sample substance contained in the barrel 160 is ejected from the needle. During an aspiration operation, the plunger 110 is drawn away from the front end 164 of the barrel 160, so that a vacuum is created, and sample (air, gas, or a liquid) that is adjacent to a front opening of a Nozzle Lumen 168 is drawn into a syringe cavity 174 (FIG. 3).

The plunger 110 includes two pair of arms: external arms 114 that extend around and, in one embodiment remain in contact with, and in another embodiment extend outside of, an outer surface of a barrel body 162, and internal arms 122 that fit within the barrel body 162. The external arms 114 and inner arms 122 are connected by an arms connector 126 at a rear (posterior) portion of the arms. A push button 112 also connects to the arms connectors 126 and serves as a thumb press for the syringe 100, when operated the injection mode of operation.

Each external arm 114 includes a front flange 118, e.g., a flange extending radially outward from each external arm 114 towards a front (anterior) end thereof in a first direction orthogonal to a longitudinal direction of the syringe 100. The front flanges 118 allow the operator to place respective forefingers on each main surface of the flange 118 and pull the plunger 110 backwards, e.g., during aspiration. Each external arm 114 optionally includes an additional pair of flanges at a middle thereof to increase a dynamic range of movement for the plunger 110 within the barrel 160. An introducer 120 is disposed at the front end of each external arm 114 to help assemble the plunger 110 with the barrel 160 during manufacturing. Moreover, a distance between respective external arms 114 is expanded when the external arms 114 are pushed over and along the outside of the barrel 160, and each introducer 120 helps to guide each external arm over the outside of the barrel 160. Generally, each introducer 120 extends along the longitudinal direction towards the anterior to be adjacent to the seal 130 (FIG. 3). Each external arm 114 may include an external arm prominence (a raised portion with cross-section) 116 that protrudes and extends in a longitudinal direction centrally along a majority thereof to strengthen the external arm 114. Each external arm 114 may have an arcuate shape in cross-section.

Each internal arm 122 may have an arcuate shape in cross-section. A gap 140 (FIG. 3) between the external arms 114 and the internal arms 122 is sufficient to accommodate a barrel body 162 of the barrel 160, as described below.

The internal arms 122 are connected to each other by a seal 130 (FIG. 3) at the front end of the plunger 110. The seal 130 may be closer to the front end of the plunger 110 than the front flanges 118. A rear surface of the seal 130 has a stopper 128 that prevents the plunger 110 from falling out when it contacts a rear circular prominence 176 (FIG. 3) of the barrel 160 when the plunger is pulled out to the maximum. A syringe seal 130 seals the air going inside or fluid going outside the syringe cavity 174. The syringe seal 130 may extend further in the syringe cavity 174 than the introducer 120 along an outside of the syringe cavity 174.

At least one edge surface of the external arms 114 includes a series of nubs 124a that are distributed along the edge at predetermined intervals and extending inwardly so as to oppose and contact an edge of external arm passage 172 when moved next to the barrel flange 170 so a movement of each nub 124a against the barrel flange 170 provides tactile feedback to an operator as the external arms 114 are urged along the barrel 160 through a passage 172, as shown in FIG. 2. At least one edge surface of the inner arms 122 includes a series of nubs 125a distributed at predetermined intervals and extending radially outward with respect to a center axis of the syringe, each nub 125a providing tactile feedback to an operator when it contacts a rear circular prominence 176 as the inner arms 122 are urged into the barrel. A reversed scale 146 may optionally be printed (with a luminescent material) onto at least one outer surface of an external arms 114 so as to allow the operator to see the scale in a darkened environment.

The barrel 160 is now described in more detail with reference to FIGS. 1 through 3. The barrel 160 includes the barrel body 162 that, with the front end 164, define the syringe cavity 174 (FIG. 3). The barrel body 160 has a generally cylindrical main body that is hollow and can optionally be tapered at the front end 164. The front end 164 inner surface matches and abuts a front surface of the seal 132. As will be discussed, the front end 164 includes a front-end breaking point 190 and a nozzle breaking point 192, which are defined regions that have grooves or other structures at predefined locations with thinner cross-sections, such that when a sufficiently large force is applied to the breaking point, the sub-component will break at that location.

An arcuate shape of the inner surface of the external arm 114 matches and abuts an outer surface of the barrel body 162, and the outer surface of the internal arm 122 is also arcuate so as to match and abut an inner surface of the barrel body 162, such that the barrel body 162 is sandwiched between the external arms 114 and internal arms 122 on opposite sides thereof. Inner surfaces of the external arms 114 are spaced slightly less than an outer diameter of the barrel body 162 such that when the external arms 114 are urged open to have a greater separation distance when extended around the barrel body 162 during assembly, a resiliency of the polypropylene material of the external arms 114 presses the external arms 114 against the barrel body 162. Similarly, the inner arms 122 are spaced such that when inserted into the barrel body 162 during assembly, a resiliency of the inner arms 122 causes the inner arms to press outwardly against an inner surface of the syringe cavity 174 (FIG. 3).

Along the surface of the barrel 160, a thermo-chemical sensor 179 is visibly present on the barrel body 162. In one embodiment the thermo-chemical sensor 179 is presented as a stick-on scale that displays a change in color to correspond with a fluid level in the syringe, assuming the fluid has a different temperature than ambient air. In one embodiment, the thermo-chemical sensor 179 is a multilayer label with stacked layer structure that includes an adhesive layer, a black blocking layer, a layer that includes liquid crystal inks separated at graduation levels on the thermo-chemical sensor 179, a white layer with graphic print (optionally printed with a luminescent material) that shows the quantity of fluid at a predetermined temperature, and a polyester clear film cover layer. The liquid crystal inks are temperature sensitive in a range of −22° F. to 240° F. One advantage of the thermo-chemical sensor 179 is that it is reversible, and so if the user is performing several aspiration and injection operations, the liquid crystal inks revert back to their original color so as to actively track the temperature of the fluid in the barrel 160 over time. A scale 177 is included on the outer surface of the barrel body 162, and may optionally be printed with a luminescent material.

A rear end of the barrel 160 is open so as to receive the plunger 110 therein. However, edges of the rear end of the barrel 160 include external arm passage 172 (FIG. 2) and barrel flanges 170 that extend radially away from the barrel 160. The external arm passage 172 is a gap between the barrel flanges 170 that allows the barrel body 162 to be inserted between the external arms 114 and the internal arms 122, while straightening a movement of the plunger 110 and preventing spiral movement of the plunger 110 by keeping the side edge of each barrel flange 170 in touch with a corresponding side of external arm 114. In particular, the external arm passage 172 is large enough to allow the front flanges 118 to pass therethrough unimpeded but also allows the barrel flange 170 to partially overlap the external arm 114 along a first direction. The barrel flanges 170 may extend radially outward along a second direction, orthogonal to the longitudinal direction of the syringe and to the first direction the front flanges 118 of the plunger 110. The barrel flanges 170 may be used for contact areas for an operator's fingers and/or thumb to control the syringe 100 during aspiration or injection.

Moreover, the pair of external arms 114 and internal arms 122 do not completely surround the barrel body, facilitating the arrangement of front flanges 118 and barrel flanges 170 that do not interfere with the front flanges 118, while the external arm passage 172 allows the barrel flanges 170 to partially overlap the external arm 114, such that movement of the plunger 110 is stably facilitated.

The barrel 160 includes an internal prominence 176 (FIG. 3), e.g., a circular or a part of a circular internal prominence, in an inner surface of a rear side on the barrel body 162. The internal prominence 176 stops the plunger 110 when a stopper 128 at a rear surface of the seal 130 contacts it, such that accidental, complete removal of the plunger 110 may be prevented.

A nozzle 166 (FIG. 1) to which a needle or a tube is to be affixed may be provided at a front end 164 of the barrel 160. The nozzle 166 may overlap the front end 164 of the barrel body 162 along the longitudinal direction. The nozzle 166 may extend further along the longitudinal direction than the front end 164. The nozzle 166 includes a nozzle lumen 168 which is the hollow bore that allows fluid to and from the syringe cavity 174 to flow therethrough.

As shown in FIG. 3, the syringe seal 130 is attached to a front end of the plunger 110 and is inserted into the rear opening of the barrel 160. The syringe seal 130 fits against the inner wall of the barrel body 162 and has a front surface that corresponds to an inner surface of the front end 164. Thus, when the plunger 110 is pressed at the push button 112 with a force directed toward the front end 164 of the barrel body, fluid in the syringe cavity 174 between the syringe seal 130 and the nozzle 166 is urged toward the nozzle 166 and emitted through the opening in the nozzle 168. If a needle is affixed to the nozzle 166, the sample is ejected from the needle. During an aspiration operation, the plunger 110 is drawn away from the barrel front end 164 so that a vacuum is created, and sample (air, gas, or a liquid) that is adjacent to the opening in the nozzle 168 is drawn into the syringe cavity 174. The syringe parts may be made from plastic, such as polypropylene for the barrel 160, and polyethene for the plunger 110. While the present embodiment uses parts made from plastic and synthetic rubber, other materials may be used as well, e.g., glass and stainless-steel barrels and/or plungers.

During an aspiration operation, the front flanges 118 and the barrel flanges 170 are engagement surfaces for fingers/thumb of the user. To aspirate, an operator's forefingers, e.g., index and middle fingers, are placed on a forward surface of plunger's front flange 118 and an operator's thumb is placed on rear surface of barrel flanges 170. When the operator pinches thumb and other forefingers together, the pinching force urges the plunger 110 to move backward, and thus withdraws the plunger 110 from the body 162 of the barrel 160. As a consequence, aspiration of the sample into the syringe cavity 174 through barrel front openings 178 is achieved.

During an injection operation, the operator places the operator's forefingers, e.g., index and middle fingers, over respective forward surfaces of the barrel flanges 170 and a thumb on the push button 112. The operator's index and middle fingers are placed directly on the barrel flange 170 so the fingers do not contact the external arms 114 of the plunger 110, which will slide forward as a result of the force exerted by pinching thumb and other forefingers together, and in turn pushes the plunger 110 forward without the operator's forefingers interfering with the movement of the plunger 110.

Figure 4:
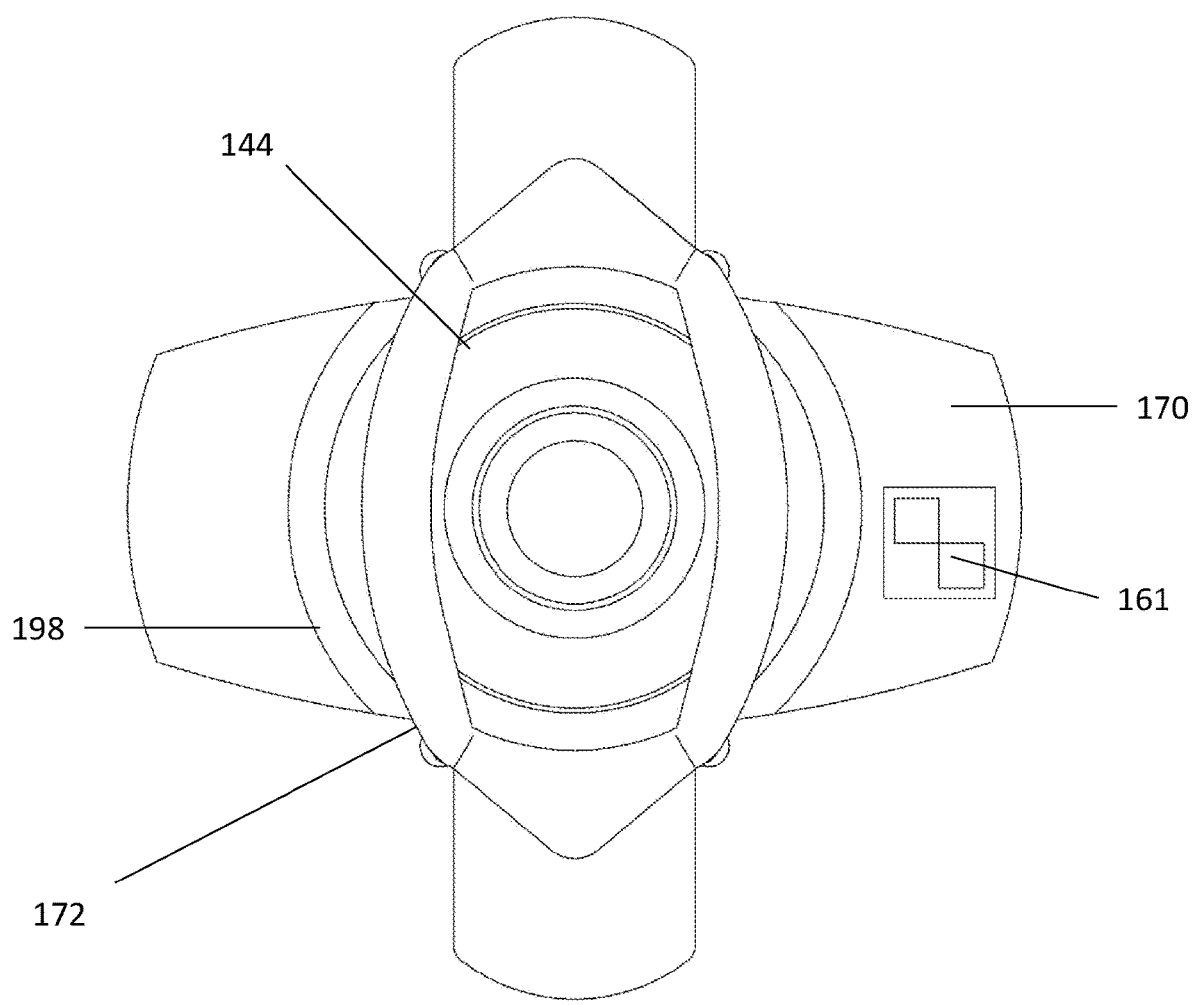
FIG. 4 is a rear view of the syringe shown in FIG. 1.

FIG. 4 is a rear view of the syringe shown in FIG. 1. For reference, push button 112 is composed of an opening 144, the rear ends of an external arm 144, the rear ends of an inner arm 122, and arms connectors. As seen, the barrel flanges 170 are shown with the external arm passages 172. Grooves formed in the barrel flanges 198 are thinned, portions of the barrel flanges 198, which are made from a heat treated polypropylene material to make the seam more brittle, such that a force of greater than 5 lb./sq-in will snap the outer portion of the barrel flanges 170 from the inner part.

In FIG. 4, a printed or active (e.g., passive/active semi-conductor device such as an RFID chip) identification item 161 is included on the barrel 160. In an embodiment where the identification item 161 is printed, it makes take the form of a bar code or a QR code. A user may use a smartphone, or bar code reader, to capture the imagine on the identification item 161, which would then take the smartphone or computer device connected to the bar code reader to a web address that contains information about the device, including a unique ID for the device. An example of such a reader is described with respect to FIG. 23. This facilitates tracking and keeping track of the syringe's location, information on the original purchaser, end user, etc. so local authorities may track down sources of syringes that are being used for nefarious reasons.

Figure 7:
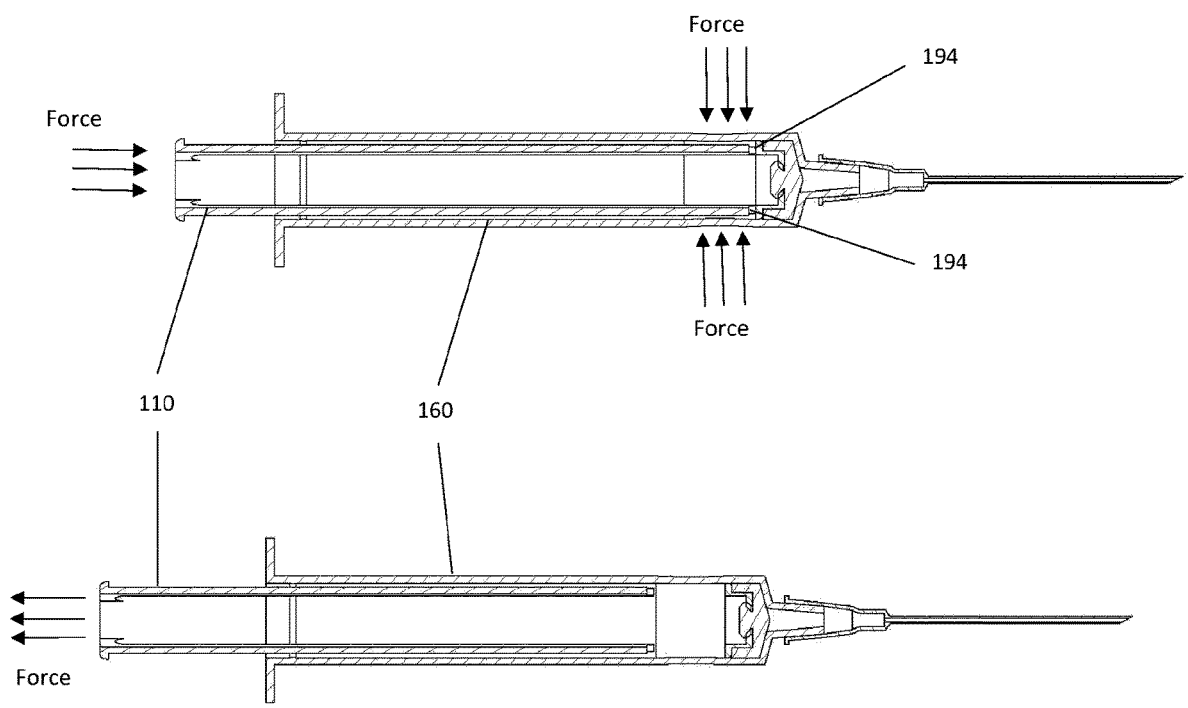
FIG. 7 shows configurations of the syringe of the embodiment in FIG. 1 before and after breaking at a seal breaking point.

FIGS. 5 to 7 show three different ways in which the syringe 100 described above is broken single handedly by the operator. In these examples, syringe 100 can be broken via three breaking points 190 (front end breaking point), 192 (nozzle breaking point), and 194 (seal breaking point). The reference to "breaking points" refers to preset weakened regions of subcomponents of the syringe 100 so that the subcomponent will break at that "point" (weakened region, such as a seam that has thinner material that surrounding material). Moreover, these recesses have a reduced cross-sectional thickness of material relative to other surrounding portions, such that when a sufficient force is applied to the body, at a distance along the body separated from the recesses, a torque experienced at the recesses causes the body to controllably break at the breaking points.

With regard to the inner arms breaking point 196 of the plunger, a proximal portion of the plunger 110, a distal portion of the plunger 110 and the inner arms breaking point 196 may be integrally molded of plastic material. The material may be made of material selected from a group of materials including polyethylene, polystyrene, polypropylene, and adhesives. The stopper and the distal end of the plunger 110 may be integrally molded of plastic material. To break the plunger 110 at the breaking point 196, a lateral force is applied on the plunger 110 several inches from the inner arms breaking point 196 while a forward end of the plunger is supported by a fixed object. This will impart a torque on the inner arms breaking point 196 that, in response to sufficiently large lateral force, will snap the plunger 110 at breaking point 196, thus breaking the plunger 110 in two pieces. The material used to make the plunger 110 is sufficiently strong to prevent breakage under normal use when only a compressive or tensile force is applied longitudinally along the plunger.

Materials for the plunger components may be one or more than one of the following representative materials: polypropylene, polyethylene, polyethyleneterephthalate (PET), polystyrene, polycarbonate, cellulosics, glass products, or combinations thereof. More expensive plastics such as polytetrafluoroethylene and other fluorinated polymers may also be used. In addition to the materials mentioned above, examples of other suitable materials include polyolefins, polyamides, polyesters, silicones, polyurethanes, epoxies, acrylics, polyacrylates, polysulfones, polymethacrylates, PEEK, polyimide, and fluoropolymers such as PTFE Teflon®, FEP Teflon®, Tefzel®, poly(vinylidene fluoride), PVDF, TOPAS® COC (cyclic olefin copolymer) and perfluoroalkoxy resins. One exemplary glass product is PYREX® (available from Corning Glass, Corning, N.Y.). Ceramic collection devices can be used according to present teachings of the disclosure.

The breaking force should not be so small as to risk unintentional activation of breakable connection during application of force during normal use or during assembly nor too great as to place undue strain on the user. Thus, a typical breaking force is between 2 lb./sq-in to 15 lb./sq-in. Accordingly, when a user presses down upon a barrel flange with the intent to disable the syringe function, a proximal portion mechanically disconnects from distal portion. The use of materials such as polypropylene, along with creases of thinned material allow for controlled breaking at particular points. The breaking points include recesses in the body (plunger/barrel). The recesses cause a cross-sectional thickness of material to be reduced relative to other portions of the body, such that when a sufficient lateral force is applied to the body, at a distance along the body separated from the recesses, a torque experienced at the recesses causes the body to controllably break at the breaking points. The breaks are clean breaks, such that the material will not merely tear or bend, but completely separate at the breaking point.

The breaking force is the total force that includes the force applied under normal use plus some additional force required to break the breakable connection, as well as the moment arm effect of applying a lateral force along a rigid body at some distance from the breaking point. The breaking force depends on various dimensions of the syringe barrel and plunger, the viscosity of the liquid being delivered, and the mechanical and hydraulic forces encountered by the filling and delivery process. If the breakable connection is too weak, the proximal portion and distal portion will separate during assembly or normal use of the collection assembly, and if the force required to break the breakable connection is too high the user may not be able to easily break the breakable connection as intended. In the present embodiment, the materials are polypropylene with heat treated grooves formed in thinned seams (0.02" to 0.05" thick) surrounded by materials of at least twice the thickness of the seams to ensure clean breaks at the breaking points.

In the embodiment of FIG. 5, once nozzle 166 (FIG. 1) with needle 199 is inserted inside a small opening that is designated for it in sharps container 1980, it can be broken at nozzle breaking point 192 by bending it to the side. Moreover, by anchoring the nozzle 166 to the opening in the sharps container 1980, and applying a lateral force of at least 2 lb./sq-in, the nozzle breaking point will give way and snap off of the barrel 160. As a consequence, the nozzle 166 and needle 199 will fall into the sharps container 1980, and the remaining part of the syringe, which is now rendered useless, may be put in the same sharps container 1980 or a different container for proper disposal.

FIGS. 6A through 6D describe another way to safely disable the syringe 100 from being re-used. FIG. 6A shows a torque being applied to a front-end breaking point 190 by imparting a downward, angled force while the needle 199 is pressed against a hard surface. As a consequence, the front-end breaking point 190 breaks on one side and the needle 199/nozzle 166 separate from the rest of the front end of syringe 164. As showing in FIG. 6B, the plunger 110 is then withdraw from the barrel 160 so there is room for the needle 199 and nozzle 166 to be accommodated within the barrel 160. As shown in FIG. 6C, the inner arms 122 are then broken at the inner arms breaking point 196. The broken part of the plunger 110 is pulled off of the barrel body 160. However, the stopper 129 of the seal holder 132 is caught by the rear circular (internal) prominence 176 so that the seal 130 serves to close-off the rear end of the barrel body 160. As shown in FIG. 6D, the broken part of plunger 110 is then turned around and the inner arms are inserted into the front end 164 of the barrel body 162 so as to close off the other end of the barrel body 162, with the needle 199 safely contained therein, the nubs of an inner arms 125a serve as stoppers so as to prevent the broken part of plunger 110 from falling out once the nub(s) are in contact with front circular prominence 178.

In the embodiment of FIG. 7, the plunger 110 is controllably broken at seal breaking point 194. In the upper portion of the figure, the plunger 110 is pushed to place the stopper 128 in front of the front circular prominence 178. Once the plunger 110 is in that forward position, an operator applies a lateral force on the barrel body 162 to break the plunger 110 at the seal breaking point 194. With a continuous lateral force, the plunger 110 is then withdrawn by pulling the plunger 110 by the operator's other hand away from the front end 164. As a consequence, the seal holder 132 is severed from the plunger 110, thus rendering the syringe 100 useless. These breaking points add a safety value by disabling the syringes, so they cannot be re-used, which, in turn, decreases risk of infection transmission that might happen with syringe re-use. Needle 199, or the entire syringe, can then be discarded in sharp containers 1980.

Figure 8:
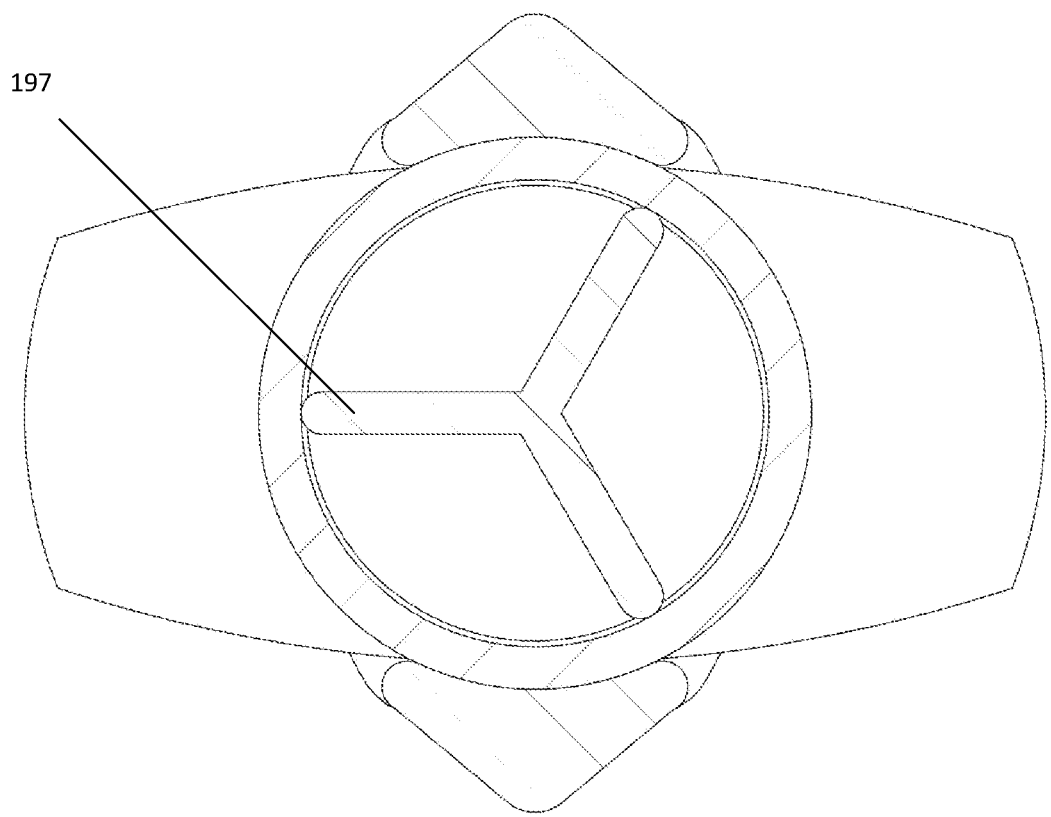
FIG. 8 is a cross section view of a syringe with a fan shape inner arm for single-handed use of a syringe, according to a second embodiment.

FIG. 8 shows the cross-section of an alternative embodiment of the embodiment of FIG. 1, as well as alternatives to other embodiments described herein with the inner arms 122 replaced with a trilateral support 197 that has three equally spaced spines that extend radially outward from a central axis. The trilateral support 197 provides a strong central rod for the plunger 110, with a straightforward structural configuration. In the embodiment of FIG. 8, a breaking point for the trilateral support 197 is formed in a similar location as for the inner arms breaking point 196, and would have a continuous groove etched, or formed, along an entire periphery of a forward end of the trilateral support 197 so the trilateral support 197 would snap at the continuous groove in response to receiving an external torque force of a predetermined amount, as discussed above.

Figure 9:
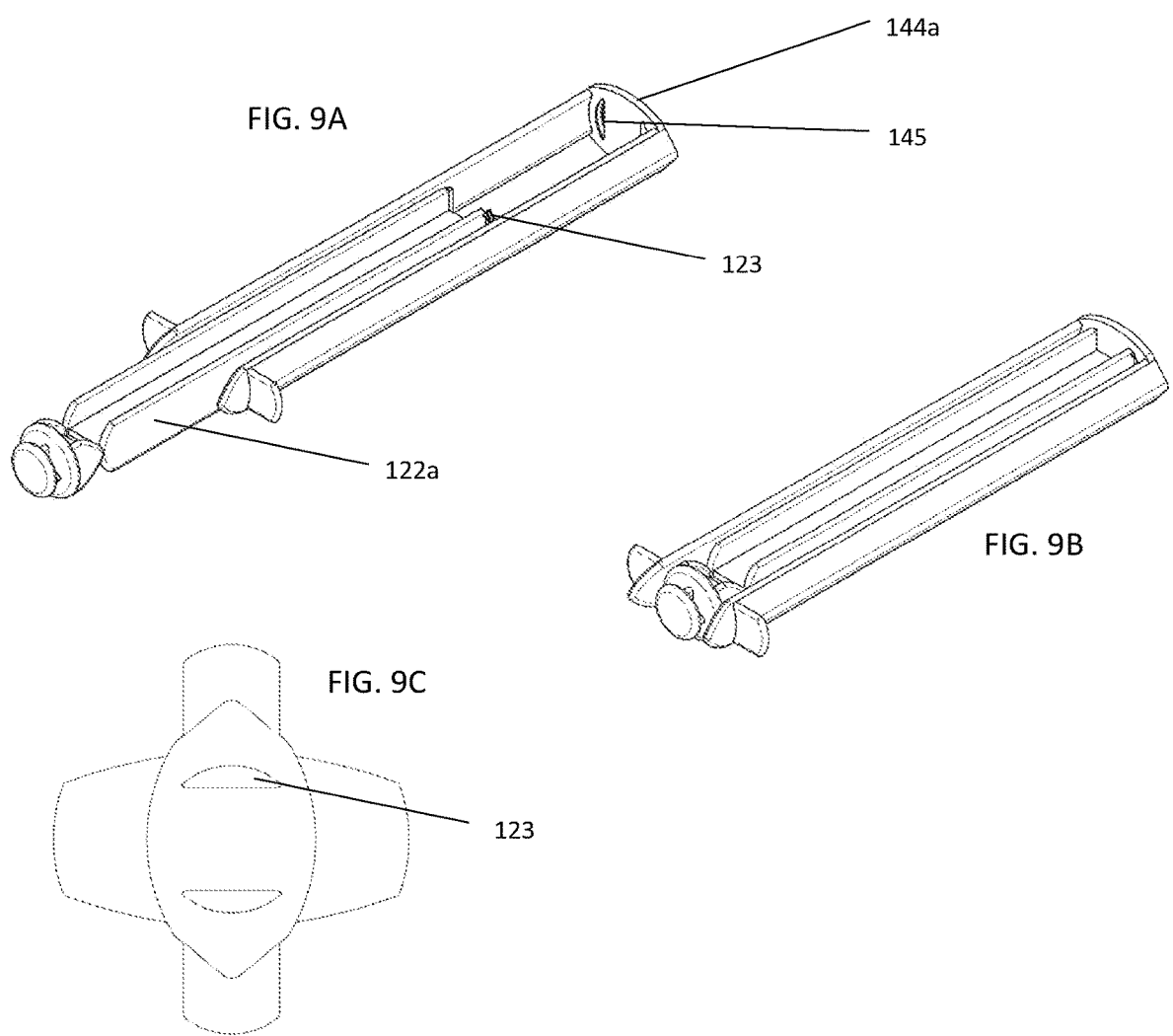
FIGS. 9A, 9B and 9C are respective views of a 2-part plunger of a syringe with an H shape inner arm and 2-part adaptable plunger for single-handed use of the syringe, according to a third embodiment.

FIG. 9A is a plunger for another embodiment that includes inner arms that detachably attach to a push button 144a with button grooves 145 formed therein. The push button 144a has button grooves 145 formed in between attachment points for the outer arms. Each inner arm 122a has an inner arm clip 123 formed at an end thereof, and each inner arm clip 123 detachably engages with the button grooves 145. FIG. 9A shows the inner arm clips 123 disengaged while FIG. 9B and FIG. 9C show the inner arm clips 123 engaged with the button grooves. In this embodiment, the inner arms 122a are formed as a pair of substantially parallel arms that are connected by a cross-member. In cross-section, the inner arms 122a and cross-member would appear as an H-beam.

Figure 10:
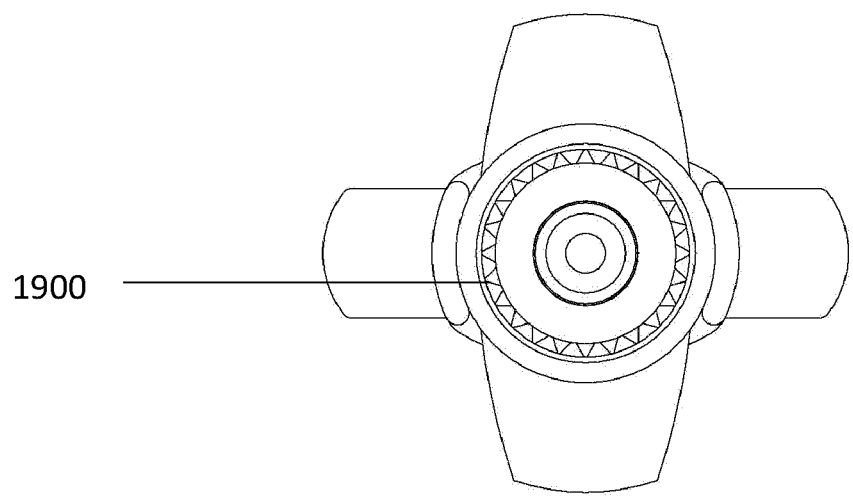
FIG. 10 is a front view of a syringe with a dual inner arm and 2-part adaptable plunger for single-handed use of the syringe, according to a fourth embodiment.

FIG. 10 is alternative embodiment to the syringe of FIG. 1, where the front end breaking point 190 is replaced with a sunshine breaking point 192. The sunshine breaking point 192 provides a serrated edge after being broken, which facilitates retaining of the plunger 110 in the forward end of the barrel 160, as shown in FIG. 6D.

Figure 11:
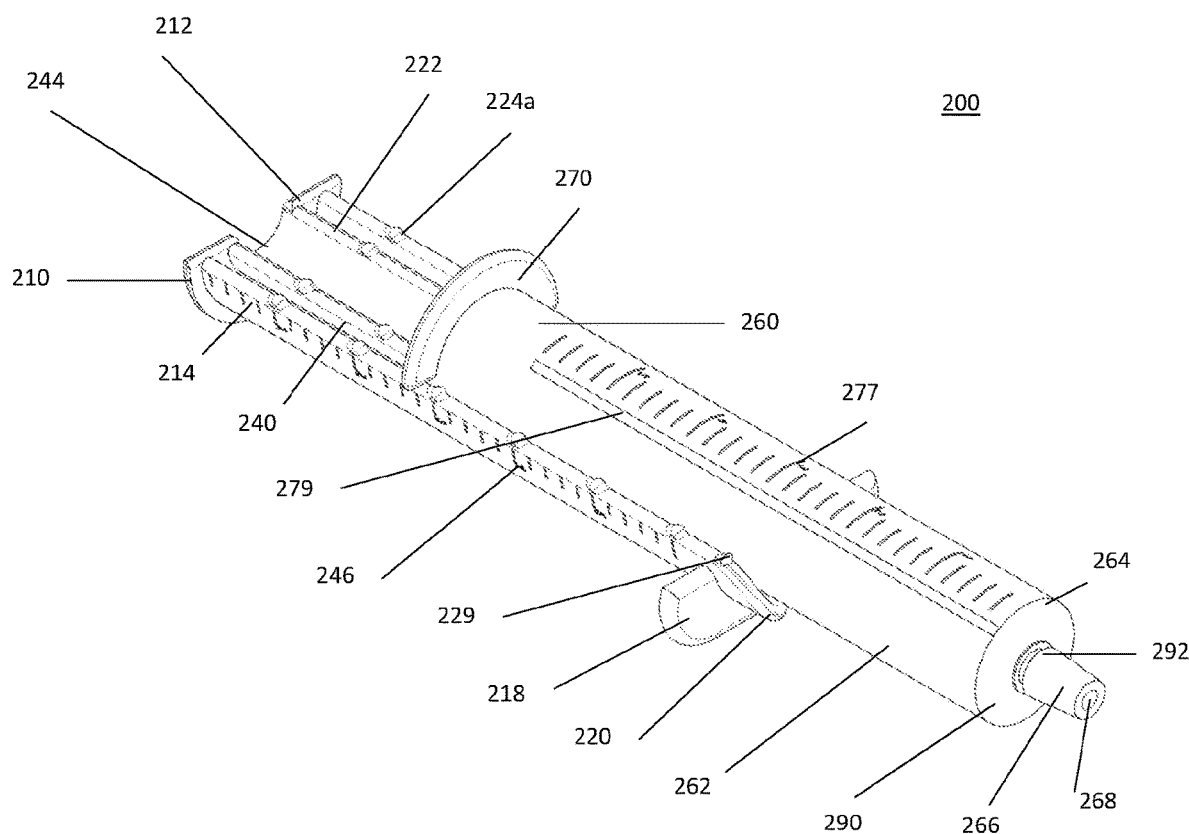
FIG. 11 is a perspective view of a syringe with semi cylindrical one-sided arms for single-handed use of the syringe, according to a modified second embodiment.
Figure 12:
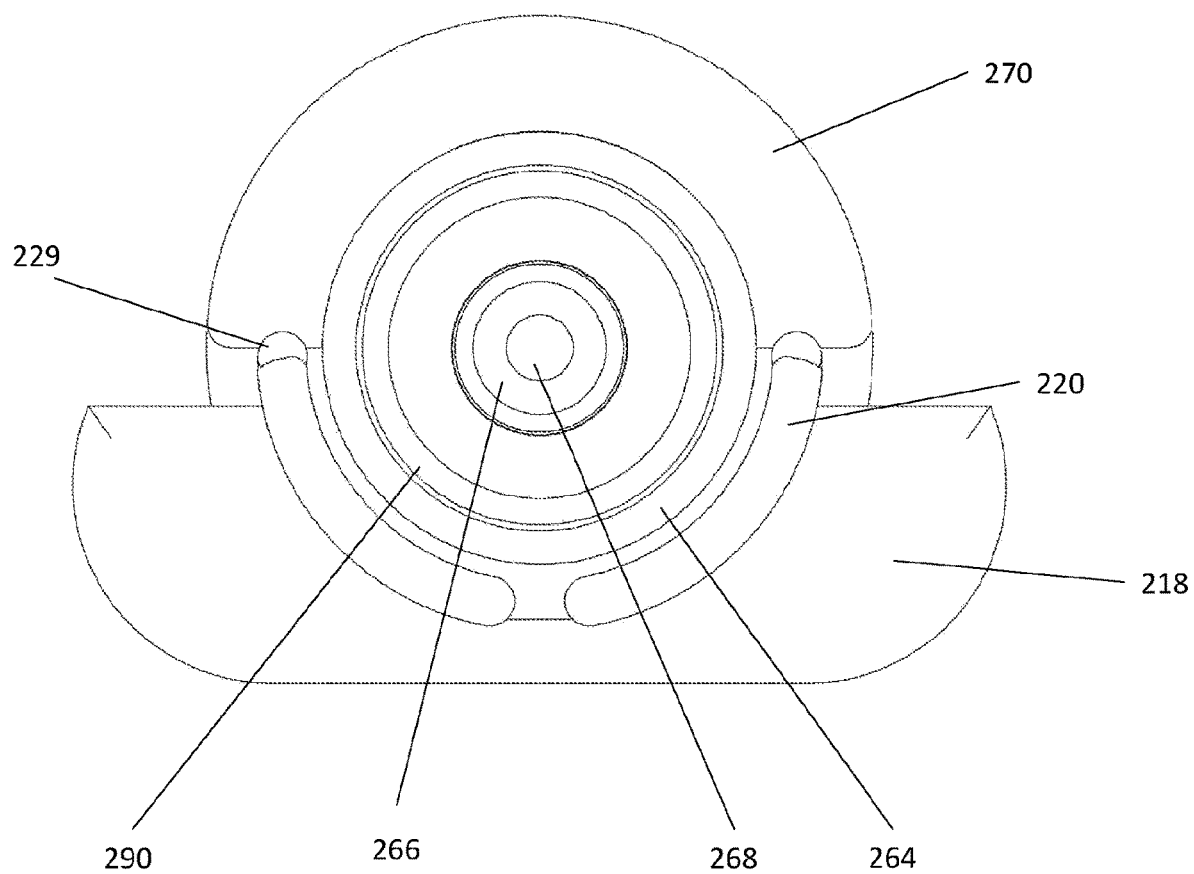
FIG. 12 is a front view of the syringe shown in FIG. 11.
Figure 13:
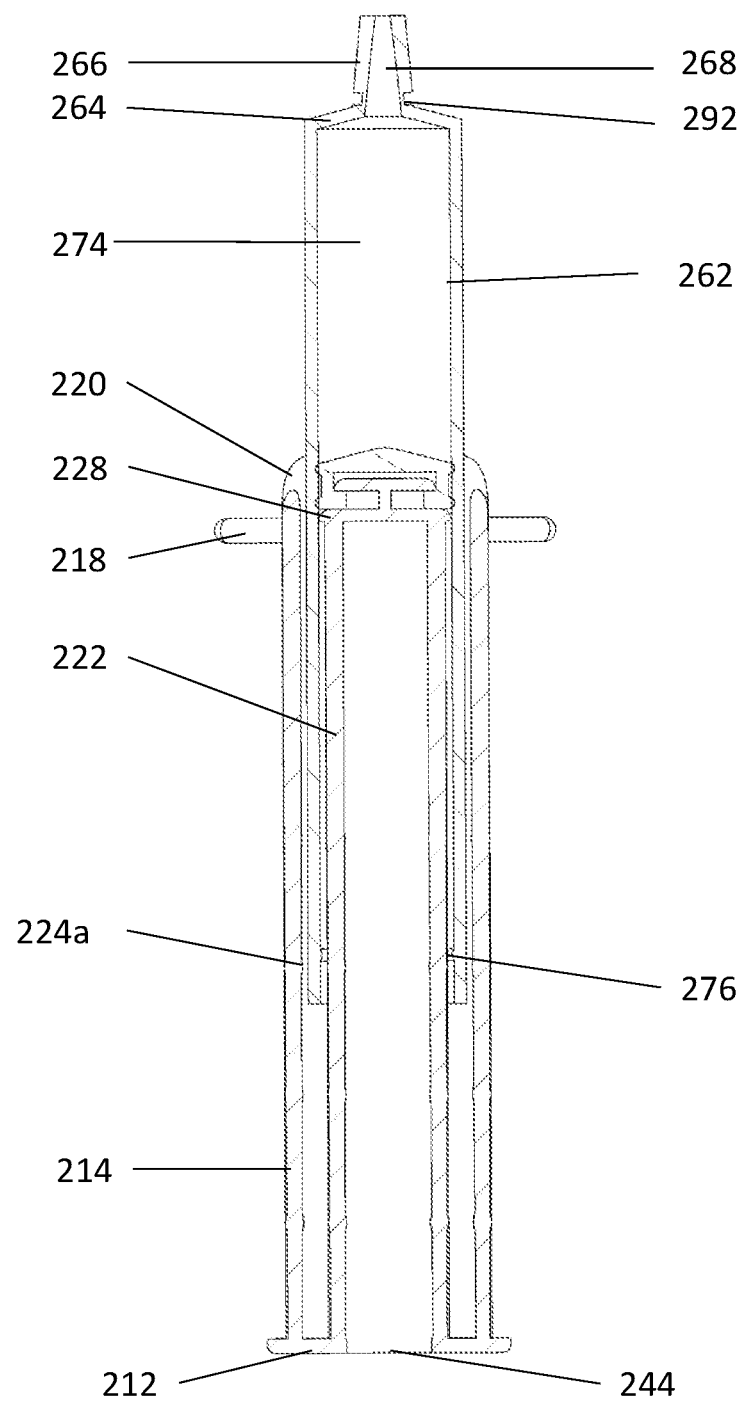
FIG. 13 is a longitudinal cross-section view of the syringe shown in FIG. 11 along a central longitudinal axis.

FIGS. 11-13 illustrate a syringe 200 according to another embodiment. The syringe 200 includes a plunger 210, a barrel 260. The parts of the syringe 200 that are the same as the parts of the first embodiment include, reversed scale 146/246, barrel body 162/262, front end 164/264, nozzle 166/266, nozzle lumen 168/268, syringe cavity 174/274, plunger breaking point, scale 177/277, external arm nubs 124a/224a, barrel breaking point 192/292, thermo-chemical sensor 179/279, rear circular prominence 176/276, front end breaking point 190/290, nozzle breaking point 192/292, which have already been discussed, and therefore further explanations of these components are not repeated or kept to a minimum.

The plunger 210 includes arcuate external arms 214 and a single, continuous arcuate internal arm 222, in contrast to the pair of arms in the previous embodiments. The external arms 214 and the internal arm 222 are in the shape of cylindrical segment, e.g., half of a cylinder. A gap 240 between the external arms and the internal arm is sufficient to accommodate a wall of barrel body 262 of the barrel 260. This is also seen in the cross sectional view illustrated in FIG. 13. The front flange 218 is a single, continuous material that generally extends away from a central axis of the barrel 260. The front flange 218 is formed on a front end and outer surface of the external arm 214, and connects and prevents the external arms 214 from deviating away (laterally) from the barrel body 262. There is a generally arcuate opening between the external arms 214, as compared with a pair of opposing flanges in the first embodiment.

At the plunger 210, the external arms 214 partially surround the barrel body 262 (by for example more or less than 180 degrees), as the external arms 214 guide the barrel body 262 when moved away from push button 212, e.g., while aspirating.

At the rear end, the plunger 210 includes the push button 212, e.g., a generally flat-shaped push button 212 including an opening 244 in an upper surface thereof extending along the inner surface of internal arm 222. The push button opening 244 is a semicircular groove on the inner side of push button 212 to decrease a chance of finger friction to push button 212, e.g., while aspirating when plunger 210 is fully inside the barrel 260.

The barrel 260 is substantially the same as the barrel 160, except for the barrel flanges 270. In this embodiment, a single, continuous generally stadium shape barrel flange 270 is provided on a side opposite the front flange 218, e.g., on an upper surface of the barrel body 262. As best seen in FIG. 12A, stopper 229 is a higher prominence than any of the nubs and is disposed on an end of the external arm 214. The stopper 229 provides a physical barrier that catches the barrel flange 270 to prevent unintentional extraction of the plunger 210 from the barrel 260. In this embodiment, the introducer 220 has a more extended arcuate shape than in the first embodiment.

Figure 14:
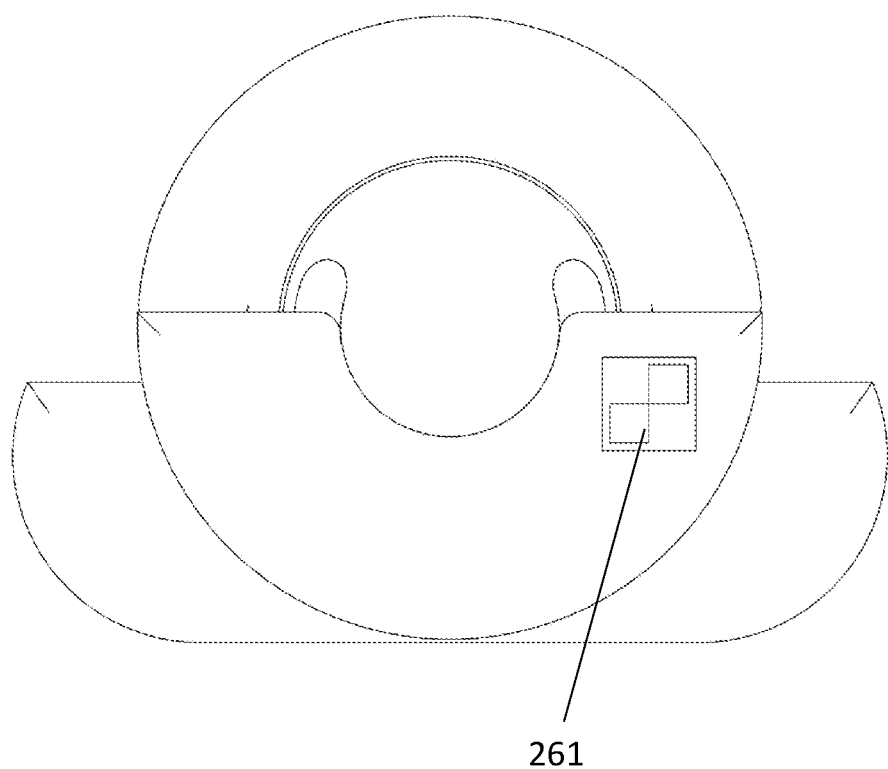
FIG. 14 is a rear view of the syringe shown in FIG. 11.

As shown in FIG. 14 an identification item 161/261 is included, in this instance on the push button 212.

The present inventor has also recognized that physicians often use a syringe in the same medical procedures as using a guidewire, such as in a Seldinger technique. However, because the syringe often requires the use of two-hands, the attending physician cannot also adequately handle the insertions or retraction of a guidewire, without assistance. In light of the recognition of this problem, the present inventor recognized the practical value in a syringe system that, in addition to enabling a singled-handed injection/aspiration function, can optionally incorporate a guidewire tract as will now be discussed.

Figure 15:
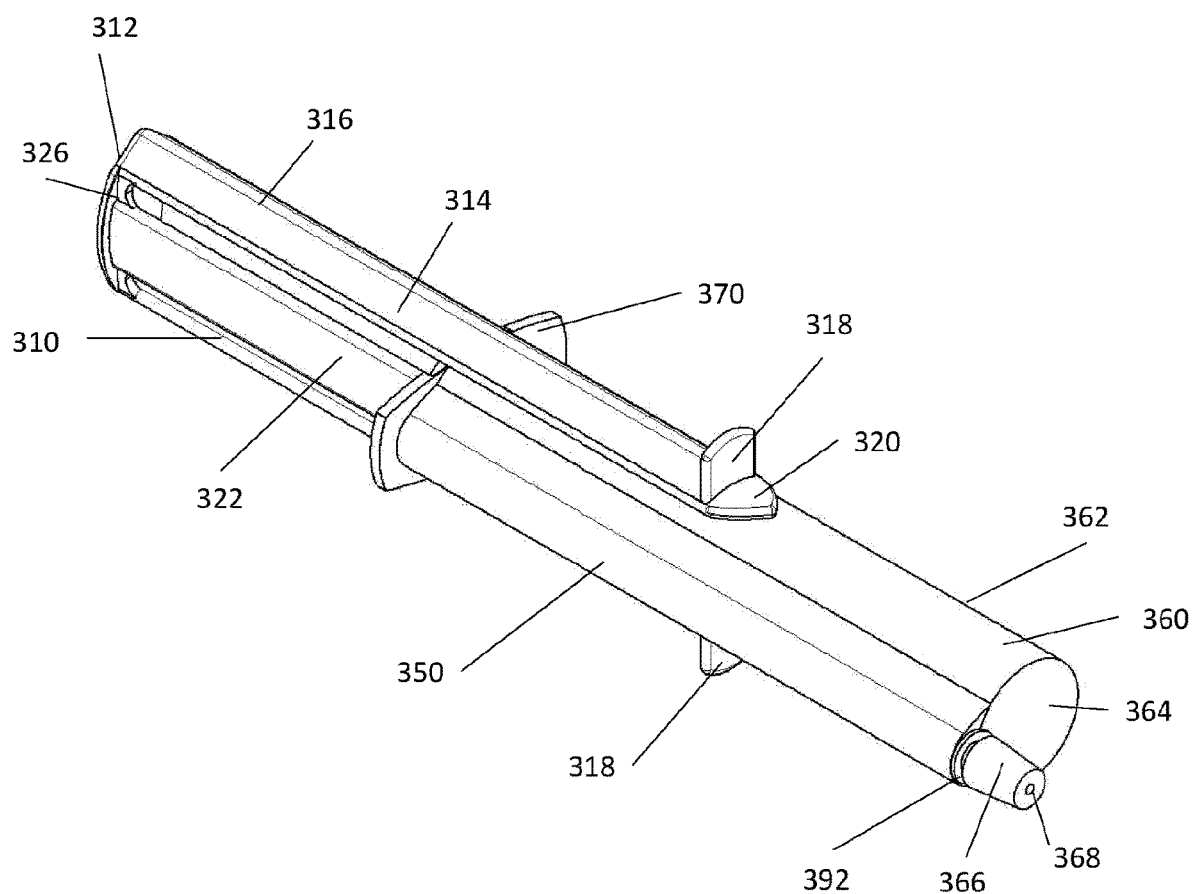
FIG. 15 is a perspective view of a syringe with a dual inner arm and a guidewire tract along the barrel for single-handed use of the syringe, according to a modified first embodiment.

FIGS. 15 to 22 illustrate syringe embodiments for single-handed injection/aspiration operation with an integrated guidewire tract and breakability features. Breaking points may be similarly included in the embodiments of FIGS. 15-22, as were previously discussed with respect to earlier described embodiments. As shown in FIG. 15, the syringe 300 includes a plunger 310, a barrel 360, and a guidewire tract 350. The parts of the syringe 300 that are the same as the parts of the first embodiment include, barrel body 162/362, front end 164/364, nozzle 166/366, nozzle lumen 168/368, syringe cavity 174/374, plunger breaking point 124/324, barrel breaking point 192/392, and rear circular prominence 176/376 are the same as the first embodiment so explanations of these components are provided above or kept to a minimum in the present explanation. During an injection operation, the plunger 310 is pressed towards a front end 364 of the barrel 360 to eject the contents (air, gas, or liquid) from the syringe cavity 374. During an aspiration operation, the plunger 310 is drawn away from the front end 364 of the barrel 360, so that a vacuum is created, and sample (air, gas, or a liquid) that is adjacent to an opening in the front end 364 is drawn into the syringe cavity 374.

The plunger 310 includes a pair of arms each including an external arm 314 and an internal arm 322, between which the barrel body 362 is to be inserted, connected by an arms connector 326 at a rear (posterior) portion thereof, e.g., a connector to strengthen the rear ends of each arm at its connection with push button 312. A push button 312 connects the arms connectors 326 for the pair of arms and serves as a thumb press for the syringe 300. The push button 312 may include an opening 344, e.g., a circular opening, for more thumb stability during injection. The inclusion of the opening 344 also reduces the material used for syringe and simplifies its manufacturability.

Figure 17:
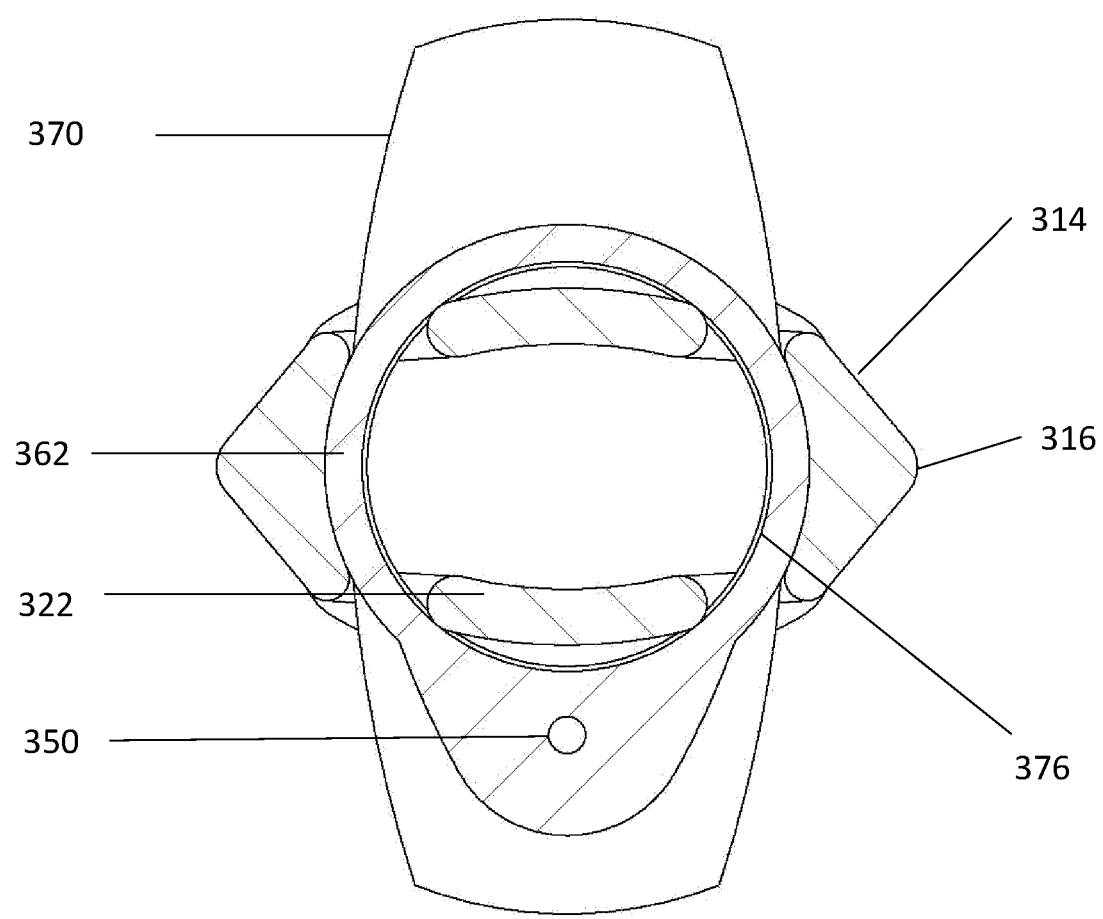
FIG. 17 is an end cross-section view of the syringe shown in FIG. 15.

Each external arm 314 includes a front flange 318, e.g., forward flanges or plunger flanges. The front flange extends radially outward from each external arm 314 towards a front (anterior) end thereof in a first direction orthogonal to a longitudinal direction of the syringe 300. While the front flange 318 is illustrated as being part of the plunger 310, the front flange may be separate from the plunger 310. The front flanges 318 allow the operator to pull the plunger 310 backwards, e.g., during aspiration. For larger syringes, an additional flange may be in the middle of each external arm 314 and has similar design of front flange 318. Each external arm 314 may include an introducer 320 at the front end thereof to help assemble the plunger 310 with the barrel 160 during manufacturing. The introducer 320 may extend along the longitudinal direction towards the anterior to be adjacent to a seal 330 of the plunger 310. As shown in FIG. 17, each external arm 314 may include an external arm spine 316 that protrudes and extends in a longitudinal direction along a majority thereof to strengthen the external arm 314, and a plunger stopper 328 on an outer surface adjacent to front flanges 318, that prevents the plunger 310 from falling out when the plunger 310 is pulled out to the maximum when stopper 328 contacts the inner circular prominence 376 of the barrel 360.

Each internal arm 322 may have an arcuate shape in cross-section. An arms gap between the external arms 314 and the internal arms 322 is sufficient to accommodate a barrel body 362 of the barrel 360, as described below. Each internal arm 322 may include nubs on protruding from outer surfaces, i.e., surfaces facing the barrel 360 but not the arms gap 340, to provide tactile sensation and feedback when the plunger moves in and out of a syringe cavity 374 and touching the inner circular prominence 376 of the barrel 360, e.g., depressing/retracting the plunger 310.

Figure 16:
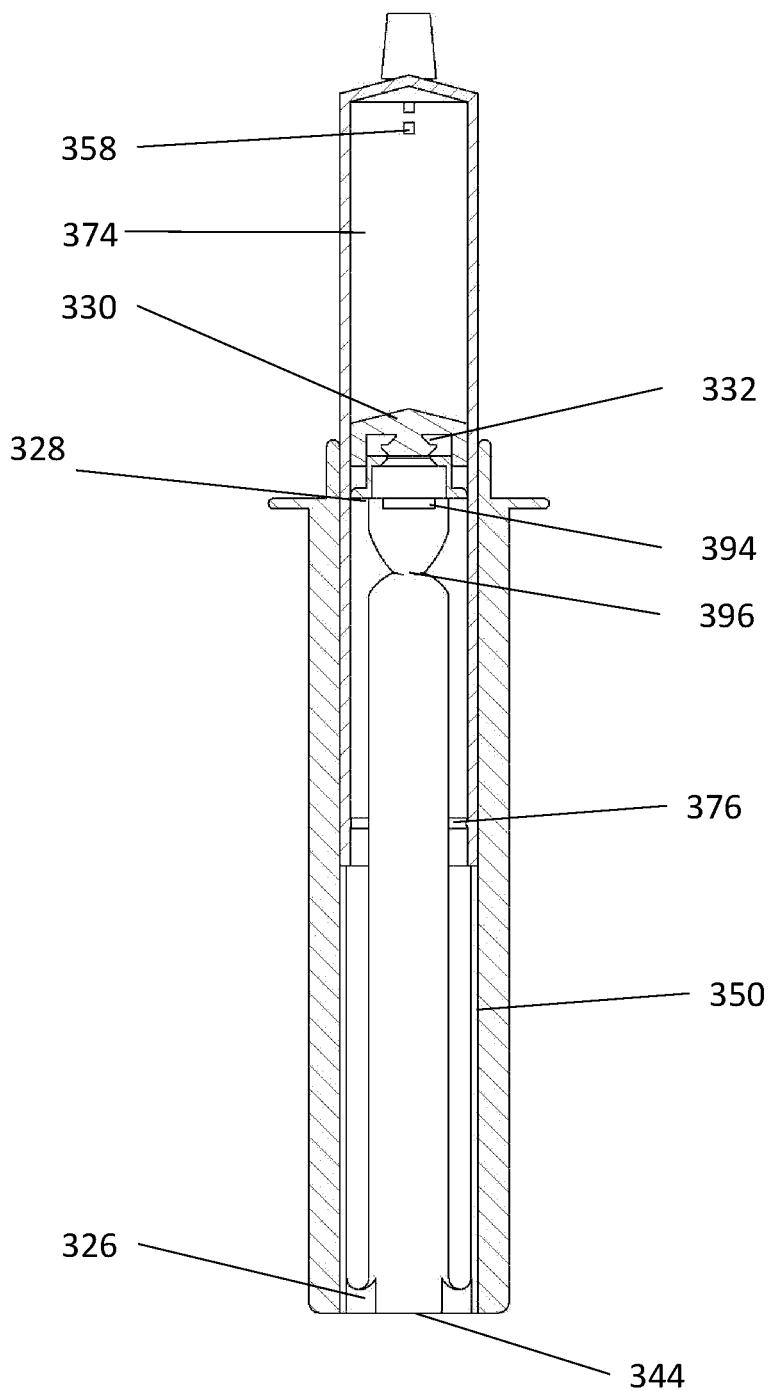
FIG. 16 is a longitudinal cross-section view of the syringe shown in FIG. 15 along a central longitudinal axis.

As shown in FIG. 16, the internal arms 322 may be connected to each other by the seal 330 at the front end of the plunger 310. The seal 330 may be closer to the front end of the plunger 310 than the front flanges 318. When rear surface of the seal 330 contacts the inner circular prominence 376 of the barrel 360, it prevents the plunger 310 from falling out when the plunger is pulled out to the maximum, i.e., the seal 330 may also serve as a stopper, in addition to the stopper 328. A syringe seal 330 seals the air going inside or fluid going outside the syringe cavity 374. The syringe seal 330 may extend further in the syringe cavity 374 than the introducer 320 along an outside of the syringe cavity 374.

The barrel 360 is substantially the same as the barrel 160, except for the addition of the guidewire tract. So, explanations of the components in barrel 360 are provided above or kept to a minimum in the present explanation. The guidewire tract will be explained in detail referencing FIGS. 15, and 18, and then later in reference to FIG. 19.

The guidewire tract 350 may be integral with the barrel body 362 and may extend along one side thereof between the pair of arms of the plunger 310 in parallel with a central longitudinal axis of the syringe barrel 360, i.e., is offset form the central longitudinal axis of the syringe barrel 360. A nozzle 366 to which a needle or a tube is to be affixed may be provided at an anterior end of the guidewire tract. The nozzle 366 may overlap, e.g., completely overlap, the guidewire tract along the longitudinal direction and may overlap, e.g., partially overlap, the front portion 364 of the barrel body 362 along the longitudinal direction. The barrel 360 includes barrel front openings 358 that are small openings to establish fluid communication between a nozzle 366 and the syringe cavity 374. Using a minimum number and a minimum size of front openings 358 that are sufficient to allow for fluid communication may help maintain the integrity and strength of the guidewire tract 350. The nozzle 366 may extend further along the longitudinal direction than the front end 364. A nozzle lumen 368 is the hollow bore that allows fluid to and from the syringe cavity 374 to flow therethrough.

Figure 18:
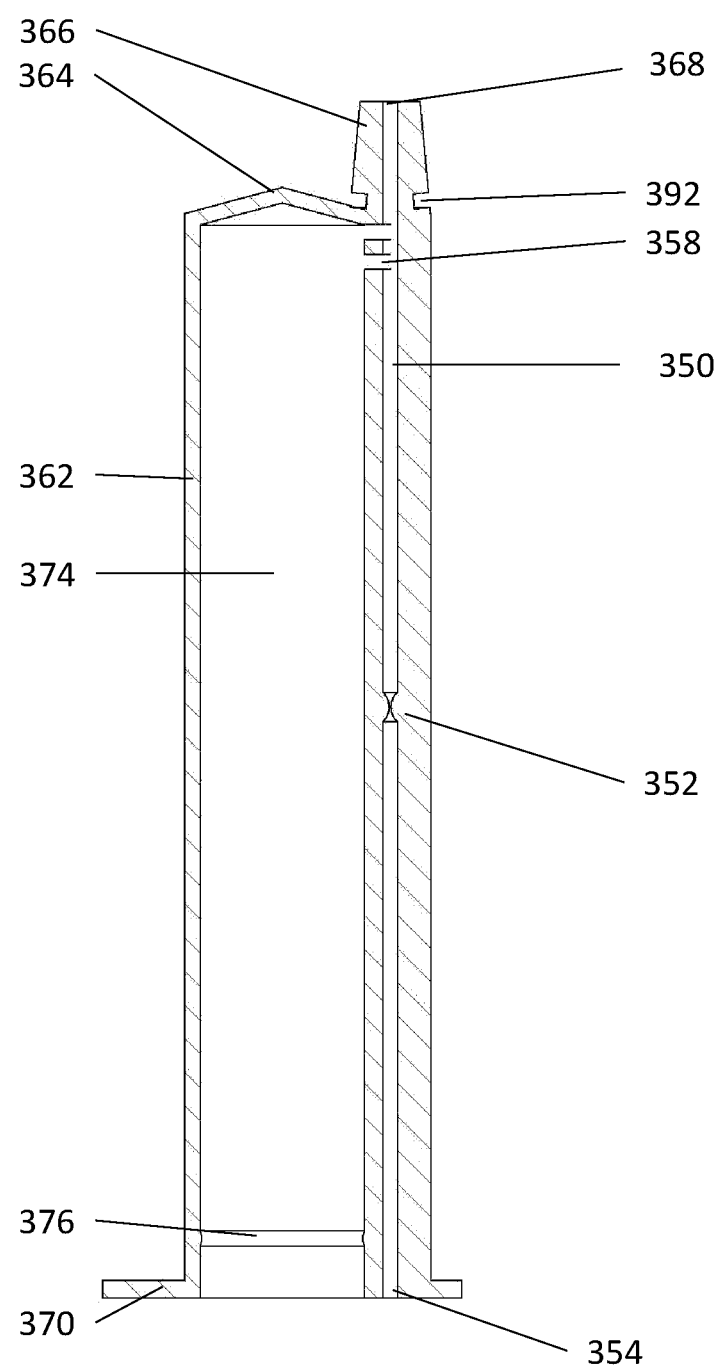
FIG. 18 is a longitudinal cross-section view of the barrel inside the syringe shown in FIG. 15 along a central longitudinal axis.

As shown in FIG. 18, the guidewire tract 350 may overlap and share the nozzle lumen 368, such that the central hollow region or tunnel that is continuous through the guidewire tract 350 and the nozzle lumen 368. The guidewire tract 350 may include a guidewire tract rear opening 354 that allows a guidewire to be inserted therein and a guidewire tract valve 352. The guidewire tract valve 352 allows the guidewire to pass therethrough, while preventing the sample in the syringe cavity 374 from leaking out of the syringe 300 through the guidewire tract 350 lumen and preventing gas from entering the syringe cavity 374 as well. The guidewire tract valve 352 may be closer to the guidewire tract rear opening 354 than to the nozzle 366.

As shown in FIG. 16, the syringe seal 330 is attached to a front end of the plunger 310 and is inserted into the syringe cavity 374. The syringe seal 330 fits to the inner wall of the barrel body 362 and has a front surface that corresponds to an inner surface of the front end 364. Thus, when the plunger 310 is pressed on the push button 312 toward the front end 364 of the barrel body, fluid in the syringe cavity 374 between the syringe seal 330 and the nozzle 366 is urged toward the nozzle 366 and emitted out of the barrel 360 toward the nozzle lumen 368. If a needle is affixed to the nozzle 366, the sample is ejected from the needle. During an aspiration operation, the plunger 310 is drawn away from the nozzle 366 so that a vacuum is created, and sample (air, gas, or a liquid) that is adjacent to the nozzle lumen 368 is drawn into the syringe cavity 374 through the front opening 378 of the barrel 360. The syringe parts may be made from plastic, such as polypropylene for the barrel 360, and polyethene for the plunger 310. While the present embodiment uses parts made from plastic and synthetic rubber, other materials may be used as well, e.g., glass and stainless-steel barrels and/or plungers.

During an aspiration operation, the front flanges 318 and the barrel flanges 370 are used by the user. To aspirate, an operator places one or more fingers, e.g., index and middle fingers, on a forward surface of the front flange 318 and a thumb on a rear surface of barrel flanges 370. When the operator pinches thumb and other fingers together, the pinching force urges the plunger 310 backwards, and thus withdraws the plunger 310 from the body 362 of the barrel 360, thus aspirating the sample inside the syringe cavity 374 through barrel front openings 378. In large sized syringes, an additional flange is added on the middle of the external arm 314, the aspiration will start when operator places one or more fingers, e.g., index and middle fingers, on a forward surface of plunger's additional flange and a thumb on a rear surface of barrel flanges 370. When the operator pinches thumb and other fingers together, the pinching force urges the plunger 310 backwards to its midway, further backward movement will happen when operator moves his fingers to be on a forward surface of front flange 318 and pinches thumb and other fingers together again, the pinching force urges the plunger 310 backwards to the end, and thus withdraws the plunger 310 from the body 362 of the barrel 360, thus aspirating the sample completely inside the syringe cavity 374 through barrel front openings 378.

During an injection operation, the operator places one or more fingers, e.g., index and middle fingers, over a forward surface of the barrel flange 370 and a thumb on the push button 312. The operator's index and middle fingers are placed directly on the barrel flange 370 so the fingers do not contact the external arms 314 of the plunger 310, which will slide forward as a result of the force exerted by pinching thumb and fingers together, which in turn pushes the plunger 310 forward without the operator's fingers interfering with the movement of the plunger 310. In large sized syringes, with an additional flange is added on the middle of the external arm 314, the injection will start when the operator places one or more fingers, e.g., index and middle fingers, over a forward surface of the barrel flange 370 and a thumb on the rear surface of additional flange which will slide forward as a result of the force exerted by pinching thumb and fingers together, which in turn pushes the plunger 310 forward to its midway, and to complete the injection, the operator moves a thumb to be on the push button 312 while the fingers e.g., index and middle fingers, are still over a forward surface of the barrel flange 370, by pinching thumb and fingers together the plunger 310 will slide forward.

In addition to allowing the operator to use one hand to operate the syringe 300 for aspiration/injection, the syringe 300 described above allows a guidewire to be passed through the guidewire tract 350 and the nozzle 366 for precise and easy handling with another hand of the operator.

FIGS. 19, 20, 21 and 22 illustrate a syringe 400 for single-handed injection/aspiration operation with an integrated guidewire tract according to another embodiment, and thus only the main differences will be highlighted.

Figure 19:
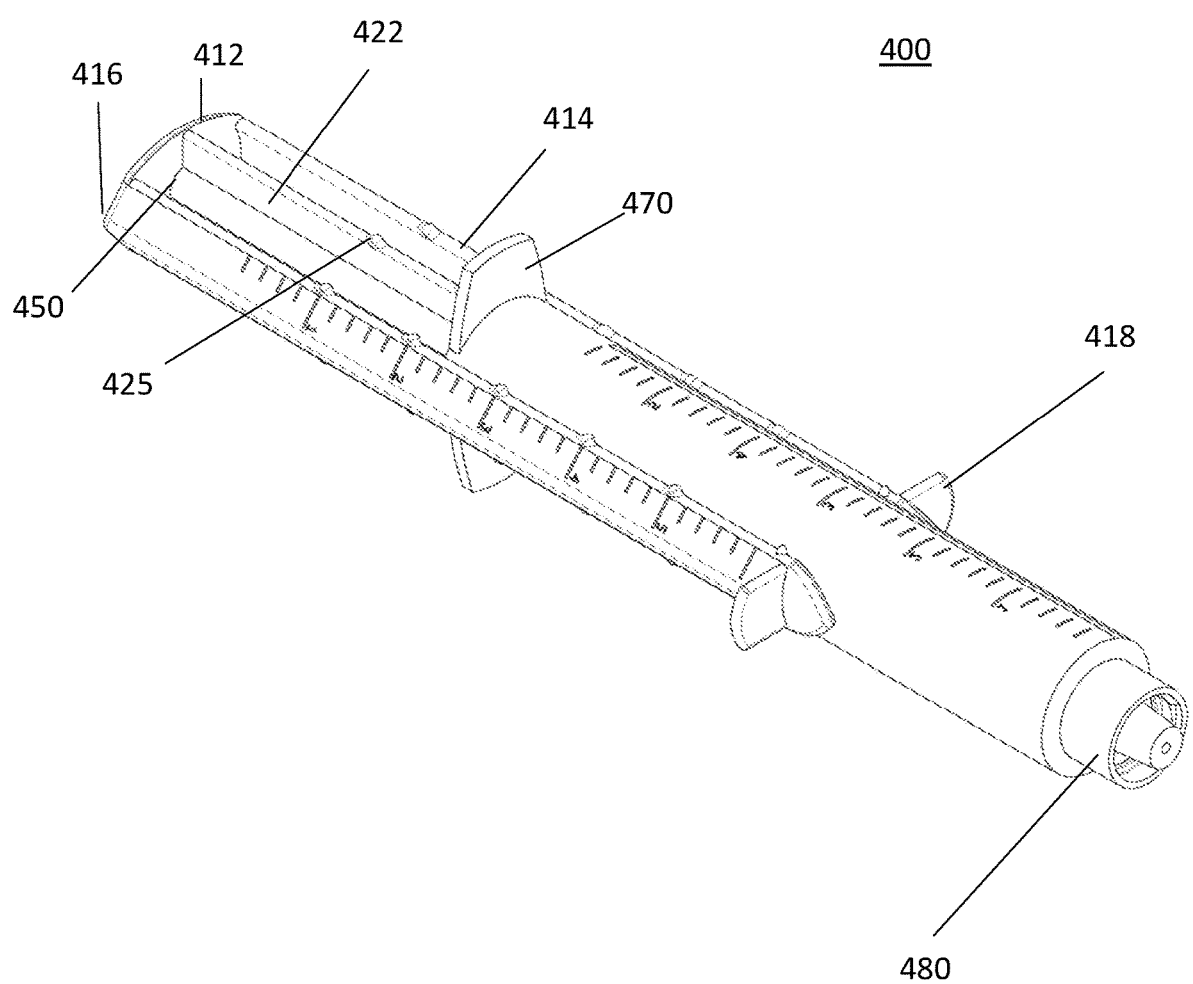
FIG. 19 is a longitudinal perspective view of a syringe with a guidewire tract within the plunger for single-handed use of the syringe, according to a modified second embodiment.

Specifically, FIG. 19 illustrates a fan shape inner arm 422 with the addition of a guidewire tract within the plunger for single-handed use of the syringe. In the second embodiment, the guidewire tract 450 (FIG. 20) is formed coaxially with the central axis of the syringe 400. A push button 412 provides a terminal surface for external arm spines 416 and the inner arm 422. Front flanges 418 and barrel flanges 470 are similar to earlier embodiments. Two external arms 414 extend around an outside of the barrel as was previously discussed. Internal arm nubs 425 are included on an outermost surface of the inner arm 422 to provide tactile feedback regarding a movement amount of the plunger within the barrel. An optional Leur lock 480 is included at a front portion of the syringe 400.

Figure 20:
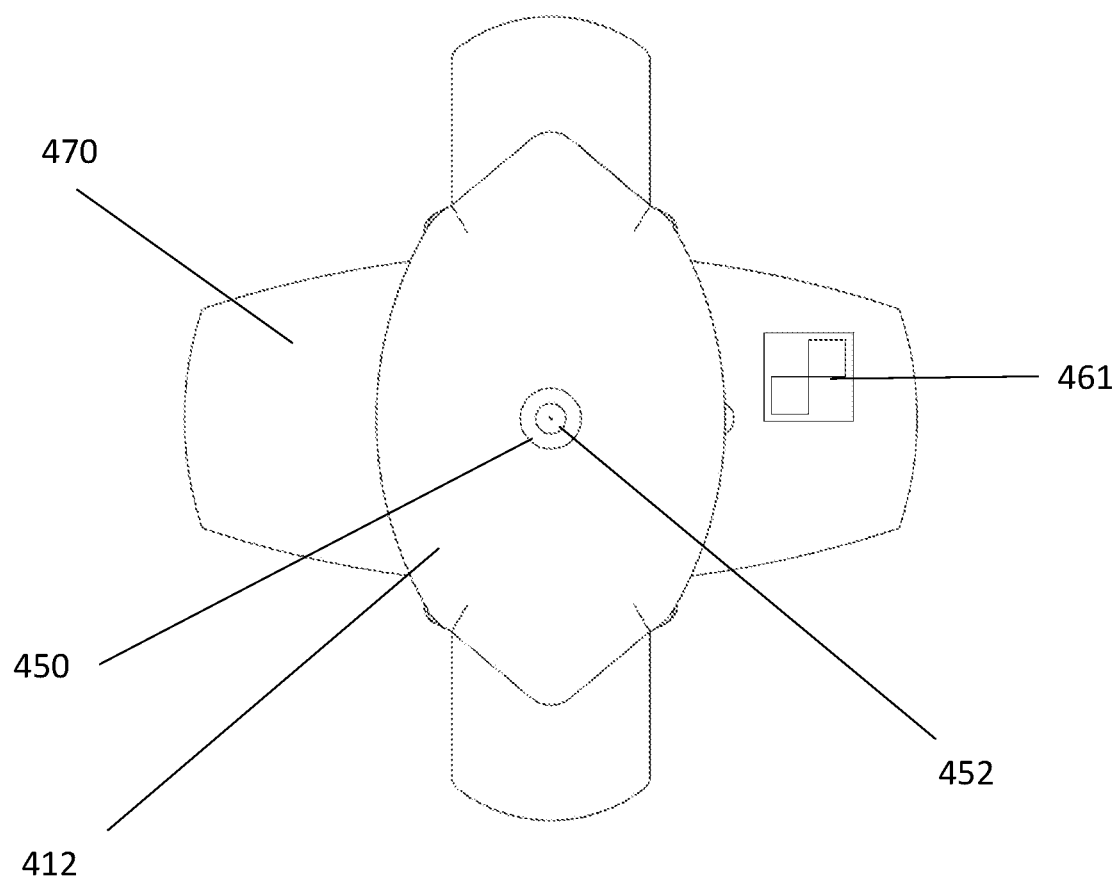
FIG. 20 is rear view of a syringe with a guidewire tract within the plunger for single-handed use of the syringe, according to a modified second embodiment.

FIG. 20 illustrates a rear view of a syringe with the addition of a guidewire tract within the plunger for single-handed use of the syringe. As shown, push button 412 has an opening for a guidewire tract 450 that is fit with a valve 452. The figure also illustrates the identification item 461 affixed to barrel flanges 470. The identification item 461 identifies the syringe, as was discussed earlier.

Figure 21:
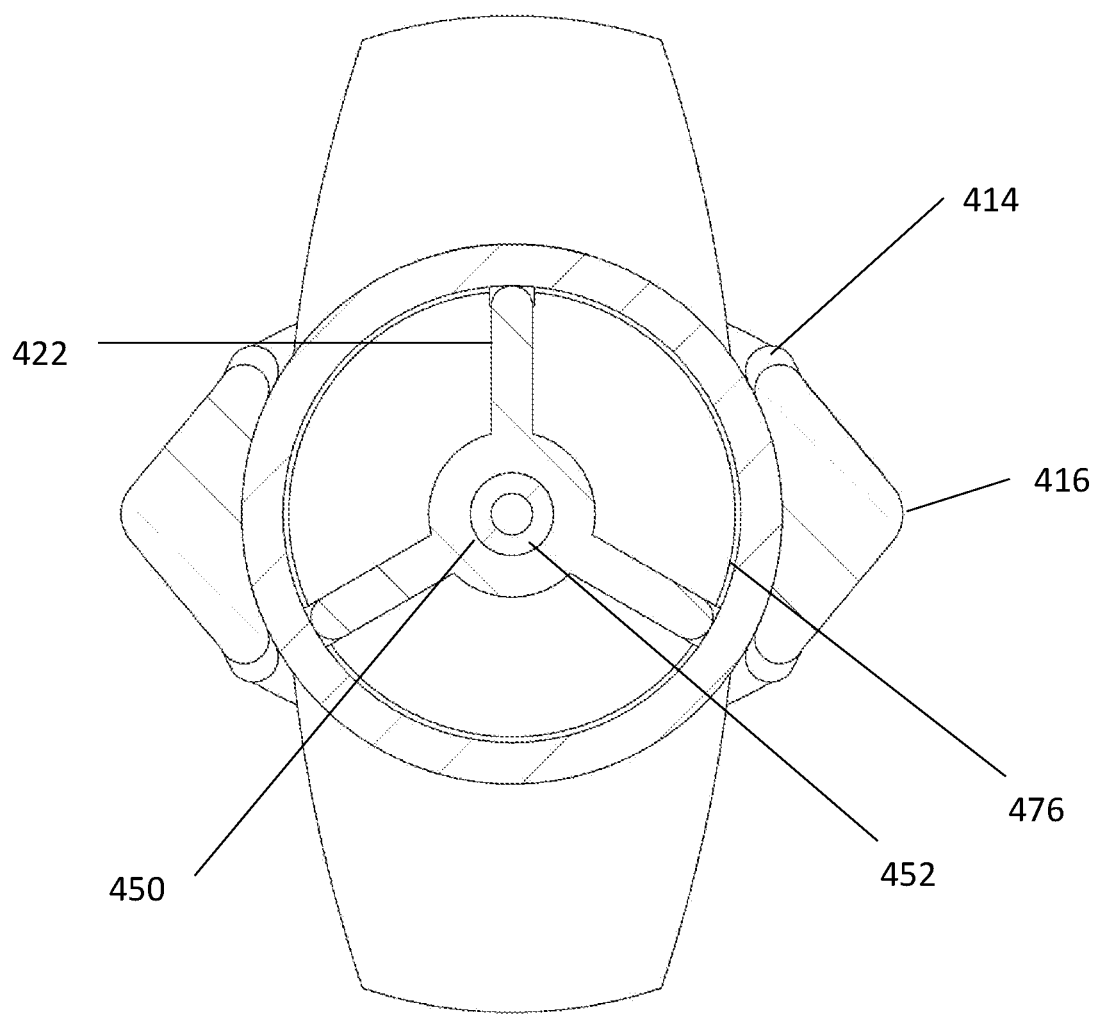
FIG. 21 is a cross section view of the syringe shown in FIG. 19.

FIG. 21 illustrates a cross section view of the syringe in which the guide tract 450 and guide wire tract valve 452 can be seen in the center of the figure. As can be seen, the guidewire tract 450 is formed in a center portion of a trilateral support 422 (inner arm). A circular prominence 476, which is similar to the inner prominences from earlier embodiments is also illustrated along with external arm 414 and external arm spine 416.

Figure 22:
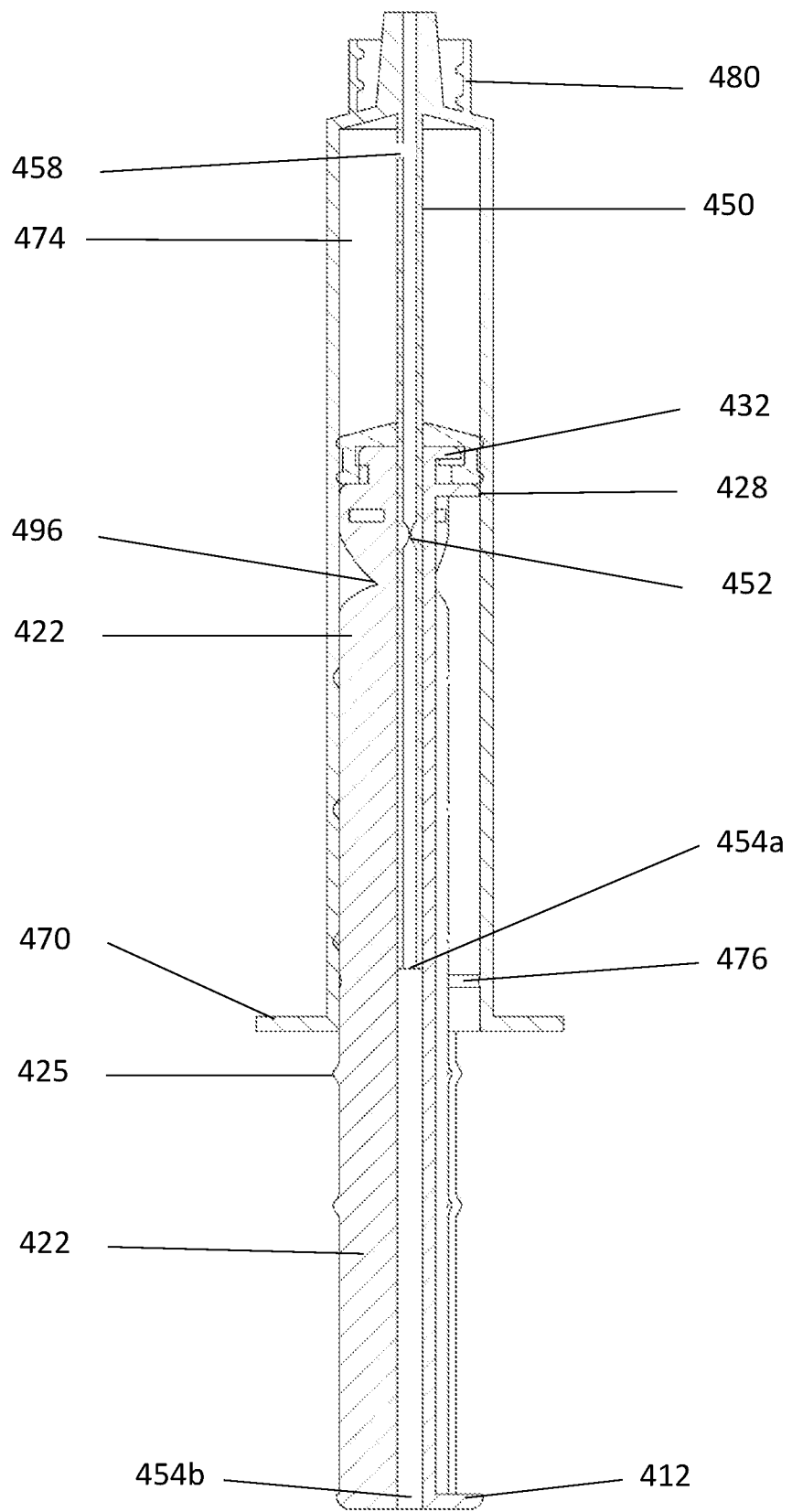
FIG. 22 is a longitudinal section view of the syringe shown in FIG. 19 along a central longitudinal axis.

As shown in FIG. 22 the guidewire tract 450 includes two portions, a plunger guidewire tract, and a barrel guidewire tract. The plunger guide wire tract includes a guidewire tract rear opening 454b, i.e., a push button 412 of the plunger includes an opening 454b, e.g., a circular opening, to allow access to the guidewire tract rear opening 454a, and a guidewire tract valve 452. The plunger guidewire tract has an inner surface that is friction fit to an outer surface of the barrel guidewire tract to allow the plunger to move readily in the barrel while allowing the guidewire to pass therethrough. The plunger and barrel guidewire tracts may be made of different materials, e.g., the plunger guidewire tract may be plastic and the barrel guidewire tract may be metal.

FIG. 22 also illustrates the Luer lock 480, guidewire tract 450 with guidewire tract front opening 458, plunger guidewire tract rear opening 454b and barrel guidewire tract rear opening 454a, with valve 452 to control leakage. A seal is mounted on seal holder 432, which includes a stopper 428 as discussed in other embodiments. A syringe cavity 474 is shown as a hollow portion through which the guidewire tract 450 extends. The inner arm 422 includes a breaking point 496, and nubs 425, as previously discussed. The syringe 400 includes barrel flanges 470 and a rear circular prominence 476.

With regard obtaining information about a syringe identification, such as the serial number, purchaser, manufacturer, etc., the information is retrievable with the use of the information item 161 as previously discussed. The information item 161 may hold the information itself such as in an RFID chip that is read from a computer-based reader, as will be discussed, or indirectly obtained from a remote computer facility. When the information item 161 holds the information itself, computer 805 interfaces with the information item 161 as an external device (e.g., external device 860 in FIG. 23. The form of communication may be nearfield communications via the peripheral interface 855, or through wireless communication (e.g., active/passive communication) where the information item 161 is excited by emissions from the network interface 850. However, when the information item 161 provides the information passively (e.g., such as through a QR code that activates a link to a remote server 830), the computer 805 optically detects the QR code via the peripheral interface 855, which includes an optical detector such as a CCD or CMOS image detector. Thus, the reader for retrieving the information contained in, or pointed to, the information item 161 is the computer system 800. The computer program product that retrieves the data on the information item 161 may be included in a computer readable storage medium.

The computer readable storage medium may be a tangible device that can store instructions for use by an instruction execution device (processor). The computer readable storage medium may be, for example, but is not limited to, an electronic storage device, a magnetic storage device, an optical storage device, an electromagnetic storage device, a semiconductor storage device, or any appropriate combination of these devices. A non-exhaustive list of more specific examples of the computer readable storage medium includes each of the following (and appropriate combinations): flexible disk, hard disk, solid-state drive (SSD), random access memory (RAM), read-only memory (ROM), erasable programmable read-only memory (EPROM or Flash), static random access memory (SRAM), compact disc (CD or CD-ROM), digital versatile disk (DVD) and memory card or stick. A computer readable storage medium, as used in this disclosure, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described in this disclosure can be downloaded to an appropriate computing or processing device from a computer readable storage medium or to an external computer or external storage device via a global network (i.e., the Internet), a local area network, a wide area network and/or a wireless network. The network may include copper transmission wires, optical communication fibers, wireless transmission, routers, firewalls, switches, gateway computers and/or edge servers. A network adapter card or network interface in each computing or processing device may receive computer readable program instructions from the network and forward the computer readable program instructions for storage in a computer readable storage medium within the computing or processing device.

Computer readable program instructions for carrying out operations of the present disclosure may include machine language instructions and/or microcode, which may be compiled or interpreted from source code written in any combination of one or more programming languages, including assembly language, Basic, Fortran, Java, Python, R, C, C++, C# or similar programming languages. The computer readable program instructions may execute entirely on a user's personal computer, notebook computer, tablet, or smartphone, entirely on a remote computer or computer server, or any combination of these computing devices. The remote computer or computer server may be connected to the user's device or devices through a computer network, including a local area network or a wide area network, or a global network (i.e., the Internet). In some embodiments, electronic circuitry including, for example, programmable logic circuitry, field-programmable gate arrays (FPGA), or programmable logic arrays (PLA) may execute the computer readable program instructions by using information from the computer readable program instructions to configure or customize the electronic circuitry, in order to perform aspects of the present disclosure.

Aspects of the present disclosure are described herein with reference to flow diagrams and block diagrams of methods, apparatus (systems), and computer program products according to embodiments of the disclosure. It will be understood by those skilled in the art that each block of the flow diagrams and block diagrams, and combinations of blocks in the flow diagrams and block diagrams, can be implemented by computer readable program instructions.

The computer readable program instructions that may implement the systems and methods described in this disclosure may be provided to one or more processors (and/or one or more cores within a processor) of a general purpose computer, special purpose computer, or other programmable apparatus to produce a machine, such that the instructions, which execute via the processor of the computer or other programmable apparatus, create a system for implementing the functions specified in the flow diagrams and block diagrams in the present disclosure. These computer readable program instructions may also be stored in a computer readable storage medium that can direct a computer, a programmable apparatus, and/or other devices to function in a particular manner, such that the computer readable storage medium having stored instructions is an article of manufacture including instructions which implement aspects of the functions specified in the flow diagrams and block diagrams in the present disclosure.

The computer readable program instructions may also be loaded onto a computer, other programmable apparatus, or other device to cause a series of operational steps to be performed on the computer, other programmable apparatus, or other device to produce a computer implemented process, such that the instructions which execute on the computer, other programmable apparatus, or other device implement the functions specified in the flow diagrams and block diagrams in the present disclosure.

Figure 23:
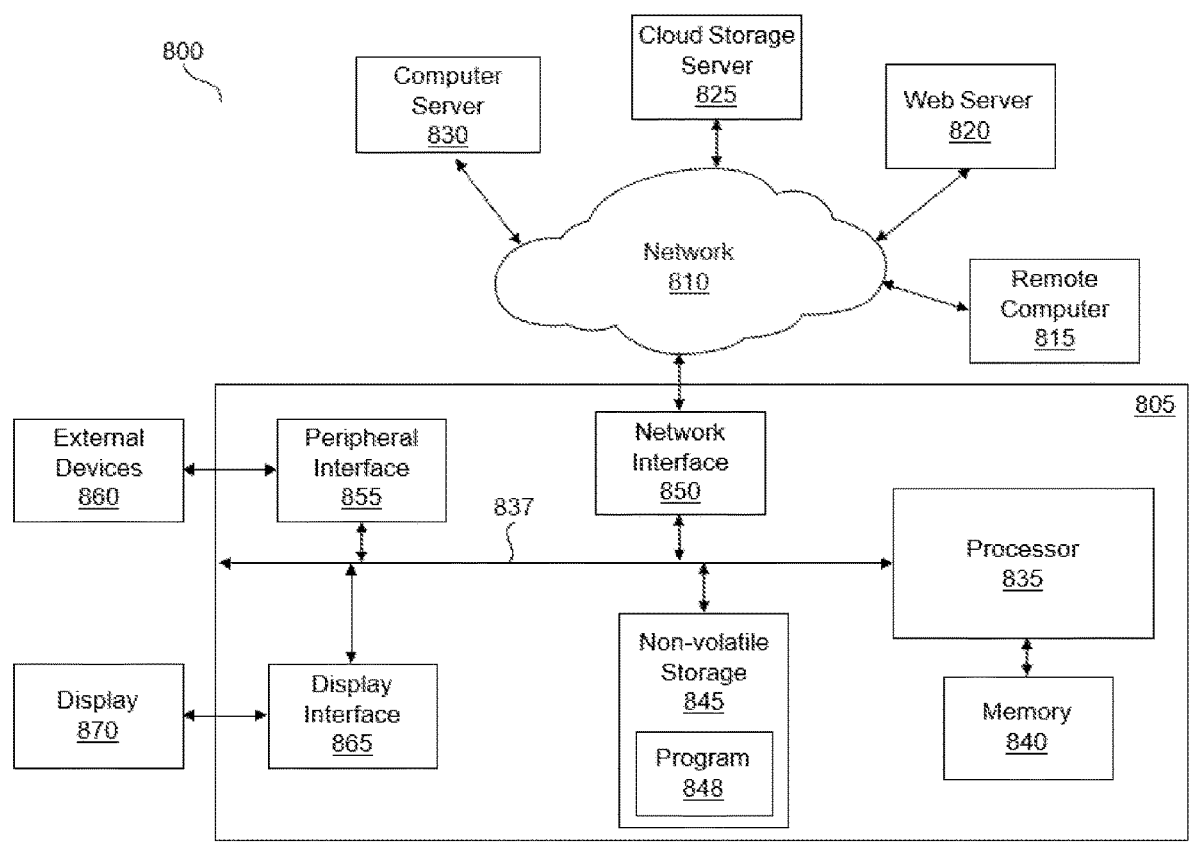
FIG. 23 is a diagram of a computer system used to record and read syringe related information from an information item contained on the syringe.

FIG. 23 is a functional block diagram illustrating a networked system 800 of one or more networked computers and servers. In an embodiment, the hardware and software environment illustrated in FIG. 23 may provide an exemplary platform for implementation of the software and/or methods according to the present disclosure.

Referring to FIG. 23, a networked system 800 may include, but is not limited to, computer 805, network 810, remote computer 815, web server 820, cloud storage server 825 and computer server 830. In some embodiments, multiple instances of one or more of the functional blocks illustrated in FIG. 23 may be employed.

Additional detail of computer 805 is shown in FIG. 23. The functional blocks illustrated within computer 805 are provided only to establish exemplary functionality and are not intended to be exhaustive. And while details are not provided for remote computer 815, web server 820, cloud storage server 825 and computer server 830, these other computers and devices may include similar functionality to that shown for computer 805.

Computer 805 may be a personal computer (PC), a desktop computer, laptop computer, tablet computer, netbook computer, a personal digital assistant (PDA), a smart phone, or any other programmable electronic device capable of communicating with other devices on network 810.

Computer 805 may include processor 835, bus 837, memory 840, non-volatile storage 845, network interface 850, peripheral interface 855 and display interface 865. Each of these functions may be implemented, in some embodiments, as individual electronic subsystems (integrated circuit chip or combination of chips and associated devices), or, in other embodiments, some combination of functions may be implemented on a single chip (sometimes called a system on chip or SoC).

Processor 835 may be one or more single or multi-chip microprocessors, such as those designed and/or manufactured by Intel Corporation, Advanced Micro Devices, Inc. (AMD), Arm Holdings (Arm), Apple Computer, etc. Examples of microprocessors include Celeron, Pentium, Core i3, Core i5 and Core i7 from Intel Corporation; Opteron, Phenom, Athlon, Turion and Ryzen from AMD; and Cortex-A, Cortex-R and Cortex-M from Arm.

Bus 837 may be a proprietary or industry standard high-speed parallel or serial peripheral interconnect bus, such as ISA, PCI, PCI Express (PCI-e), AGP, and the like.

Memory 840 and non-volatile storage 845 may be computer-readable storage media. Memory 840 may include any suitable volatile storage devices such as Dynamic Random Access Memory (DRAM) and Static Random Access Memory (SRAM). Non-volatile storage 845 may include one or more of the following: flexible disk, hard disk, solid-state drive (SSD), read-only memory (ROM), erasable programmable read-only memory (EPROM or Flash), compact disc (CD or CD-ROM), digital versatile disk (DVD) and memory card or stick.

Program 848 may be a collection of machine readable instructions and/or data that is stored in non-volatile storage 845 and is used to create, manage, and control certain software functions that are discussed in detail elsewhere in the present disclosure and illustrated in the drawings. In some embodiments, memory 840 may be considerably faster than non-volatile storage 845. In such embodiments, program 848 may be transferred from non-volatile storage 845 to memory 840 prior to execution by processor 835.

Computer 805 may be capable of communicating and interacting with other computers via network 810 through network interface 850. Network 810 may be, for example, a local area network (LAN), a wide area network (WAN) such as the Internet, or a combination of the two, and may include wired, wireless, or fiber optic connections. In general, network 810 can be any combination of connections and protocols that support communications between two or more computers and related devices.

Peripheral interface 855 may allow for input and output of data with other devices that may be connected locally with computer 805. For example, peripheral interface 855 may provide a connection to external devices 860. External devices 860 may include devices such as a keyboard, a mouse, a keypad, a touch screen, and/or other suitable input devices. External devices 860 may also include portable computer-readable storage media such as, for example, thumb drives, portable optical or magnetic disks, and memory cards. Software and data used to practice embodiments of the present disclosure, for example, program 848, may be stored on such portable computer-readable storage media. In such embodiments, software may be loaded onto non-volatile storage 845 or, alternatively, directly into memory 840 via peripheral interface 855. Peripheral interface 855 may use an industry standard connection, such as RS-232 or Universal Serial Bus (USB), to connect with external devices 860.

Display interface 865 may connect computer 805 to display 870. Display 870 may be used, in some embodiments, to present a command line or graphical user interface to a user of computer 805. Display interface 865 may connect to display 870 using one or more proprietary or industry standard connections, such as VGA, DVI, DisplayPort and HDMI.

As described above, network interface 850, provides for communications with other computing and storage systems or devices external to computer 805. Software programs and data discussed herein may be downloaded from, for example, remote computer 815, web server 820, cloud storage server 825 and computer server 830 to non-volatile storage 845 through network interface 850 and network 810. Furthermore, the systems and methods described in this disclosure may be executed by one or more computers connected to computer 805 through network interface 850 and network 810. For example, in some embodiments the systems and methods described in this disclosure may be executed by remote computer 815, computer server 830, or a combination of the interconnected computers on network 810.

Data, datasets and/or databases employed in embodiments of the systems and methods described in this disclosure may be stored and or downloaded from remote computer 815, web server 820, cloud storage server 825 and computer server 830.

Obviously, numerous modifications and variations of the present disclosure are possible in light of the above teachings. It is therefore to be understood that within the scope of the appended claims, the disclosure may be practiced otherwise than as specifically described herein.

DRAWING ELEMENTS

- 100, 200: Syringe for singlehanded operation
- 110, 210: Plunger
  - 112, 212: Push Button
  - 114, 214: External Arm
  - 116: External Arm Prominence
  - 118, 218: Front Flanges
  - 120, 220: Introducer
  - 122, 222: Internal Arm
  - 123: Inner Arm Clip
  - 124a, 224a: External Arm Nubs
  - 125a; 225a: Inner Arm Nubs
  - 126: Arms Connector
  - 129, 229: Stopper
  - 130, 230: Seal
  - 132, 232: Seal Holder
  - 140, 240: Arms Gap
  - 144, 244: Push Button Opening
  - 144a: Push Button
  - 145: Button Groove
  - 146/246: reversed scale
- 160, 260: Barrel
  - 161, 261: Identification Item
  - 162, 262: Body
  - 164, 264: Front End
  - 166, 266: Nozzle
  - 168, 268: Nozzle Lumen
  - 170, 270: Barrel Flanges
  - 172: External Arm Passage
  - 174, 274: Syringe Cavity
  - 176, 276: Rear Circular Prominence
  - 177, 277 Scale
  - 178, 278: Front Barrel Prominence
  - 179, 279: Thermo-Chemical Sensor
  - 190, 290: Front End Breaking Point
  - 192, 292: Nozzle/Barrel Breaking Point
  - 194: Seal Breaking Point
  - 196: Inner Arms Breaking Point
  - 197: Trilateral Support
  - 198: Flanges Breaking Point
  - 199: Needle
  - 1900: Sunshine Breaking Point
  - 1980: Sharps Container
- 300: Syringe for singlehanded operation including a guidewire tract
  - 312 Push Button
  - 314 External Arm
  - 316 External Arm Spine
  - 318 Front Flanges
  - 320 Introducer
  - 322 Inner Arm
  - 324 External Arm Nubs/Plunger Breaking Point
  - 325 Inner Arm Nubs
  - 326 Arms Connector
  - 328 Stopper
  - 329 External Arm Stopper
  - 330 Seal
  - 332 Seal Holder
  - 344 Push Button opening
  - 346 Reversed Scale
  - 350 Guidewire tract
  - 352 Valve
  - 354 Guidewire tract Rear opening
  - 358 Guidewire tract front opening
  - 360: Barrel:
    - 361: Identification Item
    - 362: Body
    - 364 Front End
    - 366 Nozzle
    - 368 Nozzle Lumen
    - 370 Barrel Flanges
    - 374 Syringe Cavity
    - 376 Rear Circular Prominence
    - 377 Scale
    - 379 Thermo-Chemical Sensor
    - 380 Luer Lock
    - 390 Front End Breaking Point
    - 392 Nozzle Breaking point
    - 394 Seal breaking point
    - 396 Inner Arms Breaking point
- 400: Syringe for singlehanded operation including center guidewire tract
  - 412 Push Button
  - 414 External Arm
  - 416 External Arm Spine
  - 418 Front Flanges
  - 422 Inner Arm
  - 425 Inner Arm Nubs
  - 428 Stopper
  - 432 Seal Holder
  - 450 Guidewire tract
  - 452 Valve
  - 454a Barrel Guidewire tract Rear opening
  - 454b Plunger Guidewire tract Rear opening
  - 458 Guidewire tract front opening
  - 461 Identification item (Code/Chip)
  - 470 Barrel Flanges
  - 474 Syringe Cavity
  - 476 Circular Prominence
  - 480 Leur Lock
  - 496 Inner Arms Breaking point
- 800: Networked System
  - 805: Computer
  - 810: Network 815: Remote Computer
820: Web Server
825: Cloud Storage Server
830: Computer Server
835: Processor
837: Bus
840: Memory
845: Non-Volatile Storage
850: Network Interface
855: Peripheral Interface
860: External Devices
865: Display Interface
870: Display

The invention claimed is:

1. A hand-held aspiration syringe configured for one-handed operation, comprising:
a plunger having
a seal at a forward end thereof,
a push button at a rear end thereof,
an internal plunger arm attached at a rear end thereof to the push button and to the seal at a forward end thereof,
an external plunger arm attached at a rear end thereof to the push button and to a front plunger handle at a forward end thereof, the internal plunger arm being arranged adjacent to the external plunger arm, and
wherein the front plunger handle extends radially away from the external plunger arm and having two portions separated from each other to each receive a different forefinger of a user,
a barrel having
a wall with an inner diameter that defines a hollow syringe cavity matches an outer diameter of the seal,
a nozzle formed at a forward end of the barrel through which a fluid is drawn into an inner portion of the barrel in response to the seal being drawn away from the nozzle, and
a barrel flange formed at a rear end of a hollow cylinder body of the barrel wherein at least one of the nozzle, the plunger, the barrel at a front portion thereof, and the barrel flange, and the internal plunger arm include a breaking point, the breaking point have a weaker mechanical integrity than surrounding material that breaks in response to an external force of a predetermined amount, wherein
the barrel flange comprises polypropylene having a predetermined thickness, the breaking point includes a breaking point at the barrel flange that extends from one side of the barrel flange to the other side of the barrel flange and the breaking point of the barrel flange being less thick than the predetermined thickness of the barrel flange.

2. The syringe according to claim 1, further comprising:
a semiconductor memory that contains identification information that uniquely identifies the syringe.

3. The syringe according to claim 1, further comprising:
a computer readable non-alphanumerical code that directs a computer that optically reads the computer readable non-alphanumerical code to a website having identification information about the syringe, or obtains the identification information about the syringe directly from the computer readable non-alphanumerical code.

4. The syringe according to claim 1, wherein
the breaking point includes a first breakpoint at the front portion of the barrel, and a second breakpoint at the internal plunger arm that when broken at the second breakpoint retains a portion of the internal plunger arm press-fit within the barrel to close-off a rear side of the barrel,
when broken at the first breakpoint, the nozzle, which is adapted to hold a needle, remains in the barrel, the barrel being closed at one end by the portion of the internal plunger arm press-fit within the barrel.

5. The syringe according to claim 1, wherein
an edge surface of the internal plunger arm includes a series of nubs distributed at predetermined intervals and extending radially outward with respect to a center axis of the syringe, each nub providing tactile feedback to an operator as the internal plunger arm is urged into the barrel.

6. The syringe according to claim 1, wherein
an edge surface of the internal plunger arm includes a series of nubs distributed at predetermined intervals and extending radially outward with respect to a center axis of the syringe, each nub is sized to engage a front circular prominence.

7. The syringe according to claim 1, wherein
an edge surface of the external plunger arm includes a series of nubs distributed at predetermined intervals and extending inwardly so as to oppose and contact an outer edge of the barrel flange when moved next to the barrel flange so a movement of each nub against the barrel flange provides tactile feedback to an operator as the external plunger arm is urged along the barrel through a passage.

8. The syringe according to claim 1, wherein
the barrel includes a thermo-chemical sensor along a surface of the barrel the thermo-chemical sensor being optically reactive to the fluid in the barrel such that a portion of the thermo-chemical sensor that opposes the fluid of a predetermined temperature within the barrel is one color, and another portion of the thermo-chemical sensor that does not oppose the fluid at the predetermined temperature within the barrel is another color.

9. The syringe according to claim 1, wherein
the barrel includes a visual scale providing a visual indication of an amount of the fluid in the barrel, the visual scale including one of luminescent or non-luminescent; and
the external plunger arm includes a reverse scale that is oriented in an opposite direction as the visual scale.

10. The syringe according to claim 1, wherein
the plunger includes a seal breaking point that separates a seal holder from the plunger in response to an external pinching force applied to the hollow cylinder body rear to the seal holder.

11. The syringe according to claim 1, wherein a cross-section of the plunger has a trilateral spine structure.

12. The syringe according to claim 1, wherein
the front portion of the barrel includes a front-end breaking point that is formed as a sunshine breaking point.

13. The syringe according to claim 1, wherein
the nozzle comprises polypropylene of a predetermined thickness, the nozzle includes a nozzle breaking point, wherein the nozzle breaking point comprises an annular portion around a circumference of the nozzle and being less thick than the predetermined thickness of the nozzle.

14. The syringe according to claim 1, wherein
a main body of the barrel having a predetermined thickness, the breaking point includes a breaking point at the front portion of the barrel wherein the breaking point at the front portion of the barrel comprises an annular portion on a front face of the barrel and being less thick than the predetermined thickness of the main body of the barrel; and the annular portion being a sunshine breaking point.

15. The syringe according to claim 1, wherein the plunger includes slots formed in the push button into which an end of the external plunger arm having a clip formed thereon is detachably received.

16. The syringe according to claim 1, wherein an external arm passage extends from one edge of the barrel flange to the other edge of barrel flange so as to permit the external plunger arm to pass over a rear of the hollow cylinder body and extend over an outer surface of the hollow cylinder body, and the external arm passage is contained between the edges of the barrel flange.

* * * * *